(12) United States Patent
Bowen

(10) Patent No.: US 7,973,231 B2
(45) Date of Patent: Jul. 5, 2011

(54) MUSIC SYNCHRONIZATION ARRANGEMENT

(75) Inventor: Adam Bowen, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 12/721,408

(22) Filed: Mar. 10, 2010

(65) Prior Publication Data

US 2010/0186578 A1     Jul. 29, 2010

Related U.S. Application Data

(63) Continuation of application No. 12/367,361, filed on Feb. 6, 2009, now Pat. No. 7,705,230, which is a continuation of application No. 10/997,479, filed on Nov. 24, 2004, now Pat. No. 7,521,623.

(51) Int. Cl.
*G10H 1/00* (2006.01)

(52) U.S. Cl. ................ 84/612; 84/636; 84/652; 84/668; 482/8; 482/9

(58) Field of Classification Search .................... 84/612, 84/636, 652, 668; 482/8, 9
See application file for complete search history.

(56) References Cited

U.S. PATENT DOCUMENTS

| | | | |
|---|---|---|---|
| 4,674,743 A | 6/1987 | Hirano | |
| 4,692,915 A | 9/1987 | Moriya et al. | |
| 4,776,323 A | 10/1988 | Spector | |
| 4,939,611 A | 7/1990 | Connolly | |
| 5,137,501 A | 8/1992 | Mertesdorf | |
| 5,267,942 A | 12/1993 | Saperston | |
| 5,343,871 A | 9/1994 | Bittman et al. | |
| 5,465,729 A | 11/1995 | Bittman et al. | |
| 5,533,947 A | 7/1996 | Tomlinson et al. | |

(Continued)

FOREIGN PATENT DOCUMENTS

JP       10-188452       7/1998

(Continued)

OTHER PUBLICATIONS

Toshiba Shock Sensor Roadmap PPT Slide, Toshiba America Inc., p. 1, downloaded Apr. 29, 2003: http://www.toshiba.com/taec/components/Generic/PT_ShocksensorRoadMap.htm.

(Continued)

*Primary Examiner* — David S. Warren
(74) *Attorney, Agent, or Firm* — Beyer Law Group LLP

(57) ABSTRACT

The invention generally pertains to a hand-held computing device. More particularly, the invention pertains to a computing device that is capable of controlling the speed of the music so as to affect the mood and behavior of the user during an activity such as exercise. By way of example, the speed of the music can be controlled to match the pace of the activity (synching the speed of the music to the activity of the user) or alternatively it can be controlled to drive the pace of the activity (increasing or decreasing the speed of the music to encourage a greater or lower pace). One aspect of the invention relates to adjusting the tempo (or some other attribute) of the music being outputted from the computing device. By way of example, a songs tempo may be increased or decreased before or during playing. Another aspect of the invention relates to selecting music for outputting based on tempo (or some other attribute). For example, the computing device may only play songs having a particular tempo. Yet another aspect of the invention relates to both selecting music based on tempo and adjusting the tempo of the music.

21 Claims, 13 Drawing Sheets

U.S. PATENT DOCUMENTS

| | | | |
|---|---|---|---|
| 5,592,143 | A | 1/1997 | Romney et al. |
| 5,662,117 | A | 9/1997 | Bittman |
| 5,892,573 | A | 4/1999 | Takahashi et al. |
| 5,986,200 | A | 11/1999 | Curtin |
| 6,001,048 | A | 12/1999 | Taylor |
| 6,230,047 | B1 | 5/2001 | McHugh |
| 6,582,342 | B2 | 6/2003 | Kaufman |
| 6,672,991 | B2 | 1/2004 | O'Malley |
| 6,746,247 | B2 | 6/2004 | Barton |
| 6,768,066 | B2 | 7/2004 | Wehrenberg |
| 7,038,118 | B1 | 5/2006 | Gimarc |
| 7,078,607 | B2 | 7/2006 | Alferness |
| 7,156,773 | B2 | 1/2007 | Takai et al. |
| 7,177,672 | B2 | 2/2007 | Nissila |
| 7,207,935 | B1 | 4/2007 | Lipo |
| 7,224,282 | B2 | 5/2007 | Terauchi et al. |
| 7,518,054 | B2* | 4/2009 | McKinney et al. ............. 84/612 |
| 7,659,471 | B2* | 2/2010 | Eronen ............ 84/600 |
| 2001/0015123 | A1 | 8/2001 | Nishitani et al. |
| 2001/0026413 | A1 | 10/2001 | Kisaka et al. |
| 2002/0176591 | A1* | 11/2002 | Sandborn et al. ............. 381/118 |
| 2003/0066413 | A1 | 4/2003 | Nishitani et al. |
| 2003/0159566 | A1 | 8/2003 | Sater et al. |
| 2003/0167908 | A1 | 9/2003 | Nishitani et al. |
| 2003/0221542 | A1* | 12/2003 | Kenmochi et al. ............. 84/616 |
| 2004/0044291 | A1 | 3/2004 | Yasushi et al. |
| 2004/0077934 | A1* | 4/2004 | Massad ............ 600/300 |
| 2004/0089142 | A1 | 5/2004 | Georges et al. |
| 2004/0127335 | A1 | 7/2004 | Watterson et al. |
| 2004/0143193 | A1 | 7/2004 | Nissila |
| 2004/0172481 | A1 | 9/2004 | Engstrom |
| 2004/0252397 | A1 | 12/2004 | Hodge et al. |
| 2004/0263337 | A1 | 12/2004 | Terauchi et al. |
| 2005/0126370 | A1 | 6/2005 | Takai et al. |
| 2005/0174923 | A1* | 8/2005 | Bridges ............ 369/275.3 |
| 2005/0215397 | A1 | 9/2005 | Watterson et al. |
| 2005/0215846 | A1 | 9/2005 | Elliott |
| 2005/0233859 | A1 | 10/2005 | Takai et al. |
| 2005/0252362 | A1 | 11/2005 | McHale et al. |
| 2005/0288159 | A1 | 12/2005 | Tackett |
| 2006/0088228 | A1 | 4/2006 | Marriott et al. |
| 2006/0102171 | A1 | 5/2006 | Gavish |
| 2006/0107822 | A1* | 5/2006 | Bowen ............ 84/612 |
| 2006/0111621 | A1 | 5/2006 | Coppi et al. |
| 2006/0112808 | A1 | 6/2006 | Kiiskinen et al. |
| 2006/0169125 | A1 | 8/2006 | Ashkenazi et al. |
| 2006/0185502 | A1 | 8/2006 | Nishitani et al. |
| 2006/0234832 | A1 | 10/2006 | Toyama et al. |
| 2006/0243120 | A1 | 11/2006 | Takai et al. |
| 2006/0253210 | A1* | 11/2006 | Rosenberg ............ 700/94 |
| 2006/0272480 | A1* | 12/2006 | Gimarc ............ 84/600 |
| 2006/0277474 | A1 | 12/2006 | Robarts et al. |
| 2006/0288846 | A1 | 12/2006 | Logan |
| 2006/0288849 | A1* | 12/2006 | Peeters ............ 84/616 |
| 2007/0027000 | A1 | 2/2007 | Shirai et al. |
| 2007/0033295 | A1 | 2/2007 | Marriott |
| 2007/0044641 | A1* | 3/2007 | McKinney et al. ............. 84/612 |
| 2007/0060446 | A1 | 3/2007 | Asukai et al. |
| 2007/0074617 | A1 | 4/2007 | Vergo |
| 2007/0074619 | A1 | 4/2007 | Vergo |
| 2007/0079691 | A1 | 4/2007 | Turner |
| 2007/0113725 | A1 | 5/2007 | Oliver et al. |
| 2007/0169614 | A1 | 7/2007 | Sasaki et al. |
| 2007/0186756 | A1 | 8/2007 | Sano et al. |
| 2007/0261538 | A1 | 11/2007 | Takai et al. |
| 2007/0270667 | A1 | 11/2007 | Coppi et al. |
| 2008/0013757 | A1 | 1/2008 | Carrier |
| 2008/0019223 | A1 | 1/2008 | Bridges |
| 2008/0126384 | A1 | 5/2008 | Toms et al. |
| 2008/0153671 | A1* | 6/2008 | Ogg et al. ............ 482/3 |
| 2008/0188354 | A1* | 8/2008 | Pauws et al. ............ 482/8 |
| 2008/0214358 | A1* | 9/2008 | Ogg et al. ............ 482/9 |
| 2008/0215172 | A1 | 9/2008 | Digon |
| 2008/0236369 | A1 | 10/2008 | Sasaki |
| 2008/0236370 | A1 | 10/2008 | Sasaki et al. |
| 2008/0254946 | A1* | 10/2008 | Pauws et al. ............ 482/8 |
| 2009/0044687 | A1* | 2/2009 | Sorber ............ 84/609 |
| 2009/0107320 | A1 | 4/2009 | Willacy et al. |
| 2009/0139389 | A1* | 6/2009 | Bowen ............ 84/636 |
| 2009/0271496 | A1* | 10/2009 | Nakamura et al. ............ 709/217 |
| 2009/0282020 | A1 | 11/2009 | Mcsheffrey et al. |
| 2010/0042427 | A1* | 2/2010 | Graham et al. ............ 705/1 |
| 2010/0088023 | A1* | 4/2010 | Werner ............ 701/206 |
| 2010/0186578 | A1* | 7/2010 | Bowen ............ 84/612 |

FOREIGN PATENT DOCUMENTS

| | | |
|---|---|---|
| JP | 2001-299980 | 10/2001 |
| JP | 2001-306071 | 11/2001 |
| JP | 2001-307413 | 11/2001 |
| JP | 2002-073018 | 3/2002 |
| JP | 20020739 | 3/2002 |
| JP | 2002-298496 | 10/2002 |
| JP | 2003-177749 | 6/2003 |
| JP | 2003-177750 | 6/2003 |
| JP | 2004-113552 | 4/2004 |

OTHER PUBLICATIONS

Toshiba MK2003GAH (HDD1364) Hard Disk Drive Specifications, Toshiba America Inc., 2003, pp. 1-3.

Toshiba MK6017MAP 6.0 GB IDE 2.5' 9.5MM Notebook Hard Drive Specification, pp. 1-4, downloaded Apr. 29, 2003: http://shop.store.yahoo.com/netcomdirect/tosmk6017map.html.

HDK Acceleration Sensor, Hokuriku ACS010B specification, pp. 1-2.

MK2001MPL (HDD1212) Hard Disk Drive, Product Specification, Toshiba Storage Device Division, Toshiba Corporation, Sep. 2000.

"ADXL311—Low Cost, Ultra Compact, ±2 g, Dual Axis Accelerometer," downloaded Nov. 22, 2004, http://www.analog.com/en/prod/0,,764_800_ADXL311,00.html.

"Traktor DJ Studio 2.0 with OS X Support Shipping," Press Release dated Nov. 15, 2002, http://new.harmony-central.com/Newp/2002/Traktor-DJ-Studio-20.html.

"Traktor DJ Studio 2 Ready for iTunes and iPod," downloaded Nov. 22, 2004, http://www.native-instruments.com/index.php?id=2270&type=1.

"Treadmill Programs," downloaded Oct. 28, 2004, http://us.home.lifefitness.com/content.cfm/treadmillprograms.

"Mixing & DJ Software for the Mac," downloaded Oct. 28, 2004, http://www.mp3-mac.com/Pages/MixDJ.html.

"The Mixer," downloaded Oct. 28, 2004, http://www.dj.deft.ukgateway.net/mainpages/mixers.htm.

"Virtual DJ Studio—MP3 Mixer," downloaded Oct. 28, 2004, http://www.vdj3.com/.

"The new iTunes.," downloaded Oct. 28, 2004, http://www.apple.com/ilife/itunes/.

"Introducing GarageBand.," downloaded Oct. 28, 2004, http://www.apple.com/ilife/garageband/.

"Smooth 9.25HR Programs Designed for your Fitness Goals," downloaded Oct. 28, 2004, http://www.treadmillbynet.com/smooth925_programs.htm.

"What is music?," downloaded Oct. 28, 2004, http://www.mfiles.co.uk/other-what-is-music.htm.

"How Music Affects Your Workout," downloaded Oct. 28, 2004, http://www.tinajuanfitness.info/articles/art082897.html.

"Traktor is the best Mp3 DJ Software," downloaded May 25, 2005, http://www.dj-tips-and-tricks.com/mp3-dj-software.html.

"DJ Software Pro—Mix Vibes PRO 4," downloaded Oct. 28, 2004, http://www.mixvibes.com/pages/mixvibespro4.html.

"Active MP3 DJ Studio," downloaded Oct. 28, 2004, http://www.multimediasoft.com/amp3dj/.

"Table of Contents," Oct. 2001, No. 10, Sensors & Transducers e-Digest (S&T), downloaded Oct. 14, 2004, http://www.sensorsportal.com/HTML/DIGEST/Digest_Oct_2001.htm.

Steve, "OKI Claims Smallest 3-Axis Accelerometer," Aug. 25, 2004, downloaded Oct. 14, 2004, http://robots.net/article/1269.html.

"Phase Vocoder," downloaded Oct. 20, 2004, http://www.mti.dmu.ac.uk/EARS/Data/node325.html.

N J Bailey, "Spectral manipulation with the Phase Vocoder," Oct. 13, 1998, downloaded Oct. 20, 2004, http://sculptor.sourceforge.net/Sculptor/lj/node2.html.

The PaceMaker Plug-in v2.02, Oct. 11, 2004, downloaded Oct. 20, 2004, http://sky.prohosting.com/oparviai/pacemaker/.

"Sony 20GB Network Walkman® Hard I Player," downloaded Oct. 14, 2004, http://www.sears.com/sr/javasr/product.do?BV_SessionID=@@@@0015464848.109777....

"Sony Walkman Celebrates 25th Anniversary Milestone With the Launch of a Hard Drive Music Player," Sep. 29, 2004, Press Release, downloaded on Oct. 14, 2004, http://www.pcworld.idg.com.au/index.php/id;745457704.

Mathias Mainka, "StepMan—matching music to your moves," Jan. 2004, CG Topics.

Nick Bailey, "Issue 54: Sculptor: A Real Time Phase Vocoder," Oct. 1, 1998, Linux Journal.

"Honor for StepMan in the design competition the mVs 2004," downloaded Oct. 20, 2004, http://216.239.37.104/translate_c?hl=en&sl=de&u=http://www.innovations-report.de/htm.

U.S. Appl. No. 10/791,495, filed Mar. 1, 2004.

Szabo et al., "The Effects of Slow-And Fast-Rhythm Classical Music On Progressive Cycling To Voluntary Physical Exhaustion", Sep. 1999, The Journal of Sports Medicine and Physical Fitness, pp. 220-225.

Office Action dated Aug. 7, 2007 in U.S. Appl. No. 10/997,479.

Office Action dated Jan. 28, 2008 in U.S. Appl. No. 10/997,479.

Office Action dated Jun. 16, 2008 in U.S. Appl. No. 10/997,479.

Notice of Allowance dated Dec. 12, 2008 in U.S. Appl. No. 10/997,479.

Office Action dated Jul. 1, 2009 in U.S. Appl. No. 12/367,361.

Notice of Allowance dated Dec. 10, 2009 in U.S. Appl. No. 12/367,361.

* cited by examiner

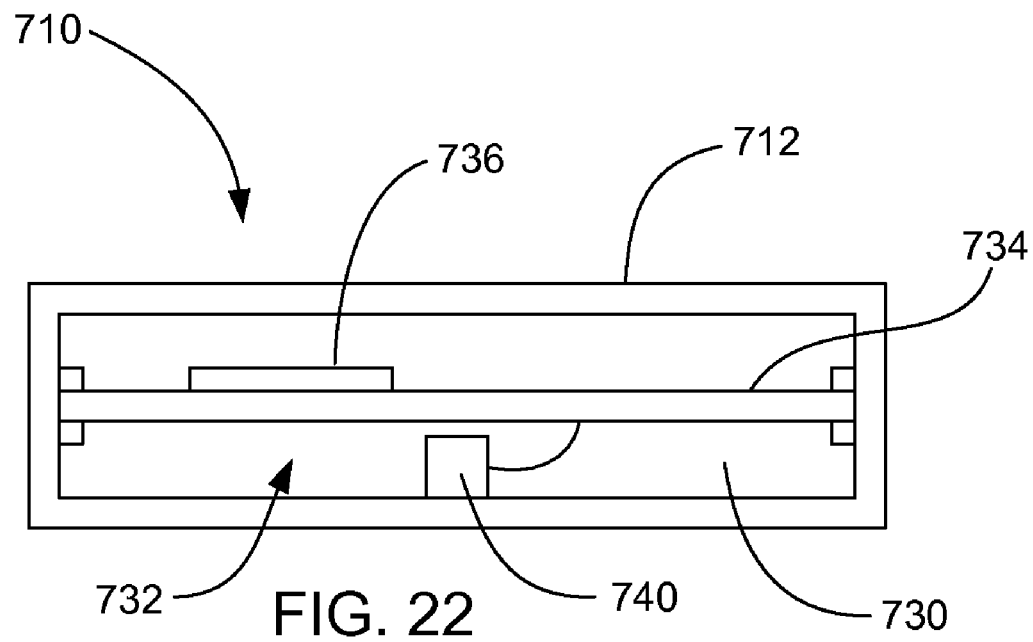
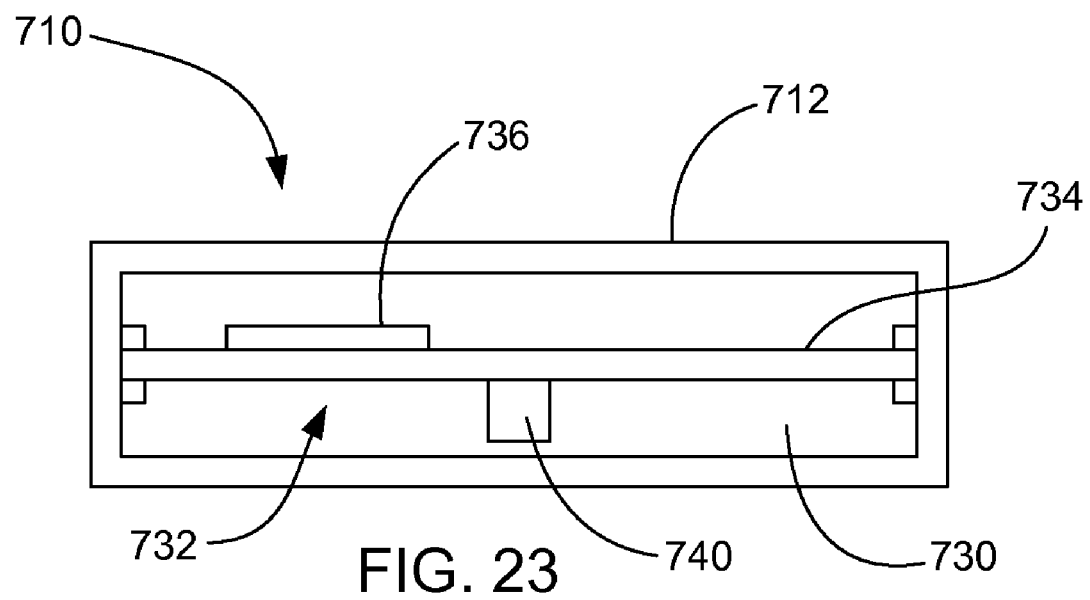

MUSIC SYNCHRONIZATION ARRANGEMENT

CROSS-REFERENCE TO RELATED APPLICATIONS

This application is a continuation of and claims priority under 35 U.S.C. §120 to U.S. patent application Ser. No. 12/367,361, filed Feb. 6, 2009 and entitled "MUSIC SYNCHRONIZATION ARRANGEMENT", now U.S. Pat. No. 7,705,230, which is a continuation of U.S. patent application Ser. No. 10/997,479 filed Nov. 24, 2004, entitled "MUSIC SYNCHRONIZATION ARRANGEMENT", now U.S. Pat. No. 7,521,623, issued Apr. 29, 2009 both of which are hereby incorporated by reference herein in their entirety.

BACKGROUND OF THE INVENTION

1. Field of the Invention

The present invention relates to portable media devices and, more particularly, to improved features for managing and outputting media items.

2. Description of the Related Art

There exist today many styles of sound machines such as home stereos, car stereos, boom boxes, CD players, and hand-held music players (e.g., MP3) for outputting music. Hand-held music players in particular have become increasingly popular as they allow a user to listen to music on the go. That is, because of their size, they can easily be transported wherever the user travels. In some cases, the devices are attached to the user, as for example, using a belt or clip, thereby making them even easier to transport. In fact, because of their ease of transport, they are commonly used when exercising. The user can wear the music player thereby leaving their hands free to exercise. The iPod® manufactured by Apple Inc. of Cupertino, Calif. is one example of a hand-held MP3 player.

In most cases, the music stored in music player is downloaded from a host device such as a personal computer. The personal computer can include music management software that allows a user to sort, store and catalog their music. More particularly, the music management software gives the user the ability to organize their music into playlists, play music, purchase music over the Internet (World Wide Web), run a visualizer to display the music in a visual form, encode or transcode music into different audio formats such as MP3, AIFF, WAV, AAC, and ALE, and transfer music between the personal computer and the music players. iTunes® manufactured by Apple Inc. of Cupertino, Calif. is one example of music management software.

A personal computer may also include other software programs associated with music. By way of example, the personal computer may utilize recording software that allows a user to perform, record and create music. These types of programs typically include features such as instruments, pre-recorded loops, amps, effects and editing tools. GarageBand® manufactured by Apple Inc. of Cupertino, Calif., is one example of a music recording program.

The personal computer may also utilize mixing software that allows a user to perform DJ mixing, live remixing, and mix recording using music in various formats such as MP3. This type of software typically performs many functions including mixing, equalizing, cross fading, looping, tempo determination, pitch and tempo adjustment, etc. In order to synchronize two songs during mixing, mixing programs may be configured to analyze the music files and create beat marks for each song (annotate all the beats of the songs so that they can be matched efficiently during mixing). Furthermore, in order to adjust the tempo of a song without affecting pitch, mixing programs may utilize a technique called phase vocoding, which is one of the more powerful methods of manipulating sounds in the frequency domain. Only recently have personal computers had sufficient processing to make real-time phase vocoding a viable proposition. In the past, algorithms for phase vocoding were of such complexity and personal computers were of limited processing power such that it would often require many hours of processing to acquire each second of audio output. Traktor DJ Studio 2.0 manufactured by Native Instruments of Germany is one example of a mixing program.

Although music player systems utilizing a music player and personal computer work well, there is a continuing need for improved features for managing and outputting music.

SUMMARY OF THE INVENTION

The invention relates, in one embodiment, to a music method performed on a hand-held computing device. The method generally includes designating an attribute of a song. The method also includes controlling the music output of the computing device based on the designated attribute of the song. The attribute may, for example, correspond to the tempo of the song.

The invention relates, in another embodiment, to a method performed on a hand-held computing device. The method includes designating a tempo. The method also includes adjusting the tempo of one or more audio tracks being outputted to match the designated tempo.

The invention relates, in another embodiment, to a method performed on a hand-held computing device. The method includes storing a plurality of audio tracks. Each audio track having a tempo. The method also includes designating a tempo. The method further includes selecting audio tracks from storage with a tempo similar to the designated tempo.

The invention relates, in another embodiment, to a computer readable medium contained on a hand-held music player and including at least computer code for managing music. The medium includes obtaining the tempo of an event. The medium also includes outputting music. The medium further includes controlling the tempo of the music being outputted based on the tempo of the event.

The invention relates, in another embodiment, to a hand-held media player. The hand-held media player includes a housing of the media player. The hand-held media player also includes an accelerometer disposed inside the housing of the media player and configured to measure the motion of the media player. The hand-held music player further includes a music storage element disposed inside the housing of the media player and configured to contain one or more music items. The hand-held media player additionally includes a processor disposed inside the housing of the media player, and operatively coupled to the accelerometer and the music storage element. The processor is configured to control the output of the music items based on the motion of the media player.

The invention relates, in another embodiment, to a method performed on a hand-held media player. The method includes sensing the pace of body motion. The method also includes playing one or more audio tracks. The method further includes adjusting the tempo of each audio track in accordance with changes in body motion.

The invention relates, in another embodiment, to a method performed on a hand-held music player. The method includes designating a tempo profile. The method also includes outputting one or more audio tracks. The method further includes adjusting the tempo of the audio tracks based on the tempo profile.

The invention relates, in another embodiment, to a method of transferring data between a host device and a portable media device. The portable media device is capable of storing and playing media items. The method includes, at the host device, designating at least one audio file for downloading to the portable media device. The method also includes, at the host device, generating a tempo tag for each designated audio file. Each tempo tag indicates the tempo of the audio file. The method further includes, at the host device, sending the audio file including the tempo tag to the portable media device.

The invention relates, in another embodiment, to a method of transferring data between a host device and a portable media device. The portable media device is capable of storing and playing media items. The method includes, at the host device, designating at least one song for downloading to the portable media device. The method also includes, at the host device, producing a music collection for each designated song. Each music collection contains the original version of the designated song and new versions of the designated song. Each new version has a different tempo. The method further includes, at the host device, sending the music collection to the portable media device.

The invention relates, in another embodiment, to an operational method for a hand-held music player. The method includes storing music data. The music data includes a plurality of music collections. Each music collection contains an original song and a plurality of differently formatted songs based on the original song. The original and differently formatted songs have different tempos. The music collection is generated separately on a device other than the portable media device. The method also includes designating a desired tempo. The method further includes retrieving at least one song from storage having a tempo that closely matches the desired tempo. The method additionally includes outputting one or more of the retrieved songs.

The invention relates, in another embodiment, to a portable media device capable of playing music. The portable media device includes a storage device containing downloaded music data. The music data includes a plurality of music collections. Each music collection includes an original song and plurality of different versions of the original song. Each song in the music collection has an attribute with a different value. The portable media device also includes a processor configured to control the supply of songs to a speaker.

BRIEF DESCRIPTION OF THE DRAWINGS

The invention will be readily understood by the following detailed description in conjunction with the accompanying drawings, wherein like reference numerals designate like structural elements, and in which:

FIG. 22 is a side elevation view of a hand-held computing device, in accordance with one embodiment of the present invention.

FIG. 23 is a side elevation view of a hand-held computing device, in accordance with one embodiment of the present invention.

DETAILED DESCRIPTION OF THE INVENTION

Figure 1:
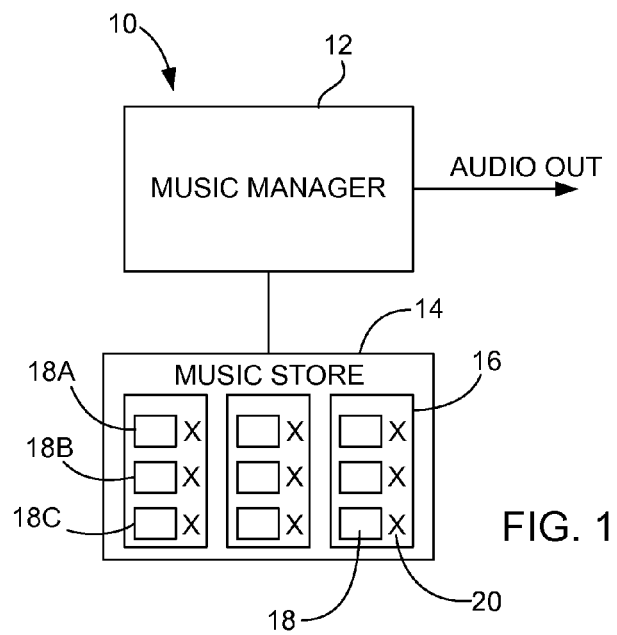
FIG. 1 is a simplified block diagram of a music player, in accordance with one embodiment of the present invention.

It is well documented that music can affect the mood and behavior of people. For example, different compositions of music may be used for relaxing, romancing, dancing, exercising, etc. During exercise in particular, music can be used to motivate, speed and drive the intensity of the workout. For example, it is generally believed that if the music is invigorating and inspiring people will be more motivated to work out. Because of this, most gyms play music with an upbeat tempo to keep people motivated during their work out. Furthermore, some studies have shown that joggers who exercised with music had greater endurance, worked out longer and felt better about the workout than those who worked out without music.

One attribute of music that is believed to be tied strongly to mood and behavior is tempo. Tempo, which is often measured in beats per minute (bpm), is the speed at which an element or composition is played. The tempo of music typically ranges between 50 and 200 beats per minute. Although tempo sets the basic pace of music, it should be noted that the rhythm of the music can also have an impact on the perceived pace (so it too can affect a person's mood and behavior).

With regards to exercising, it is generally believe that the speed of the music influences the pace of a person's workouts since the body automatically tries to keep in synch with the music. Because of this, slower tempos, which tend to produce a more relaxed state, are typically used when stretching, warming up or cooling down, while faster tempos, which tend to produce a more excited state, are typically used when strength training or performing cardio work outs. In fact, some studies have shown that sedative music (low tempo) is great for stretching but bad for strength training, and that stimulating music (high tempo) is good for strength training but bad for stretching.

The invention generally pertains to a hand-held music player. The term hand-held music player is primarily directed at music storage players such as MP3 music players, although it may also be directed at any hand-held personal computing device capable of outputting music as, for example, a game player, a video player, a cell phone, a personal digital assistant (PDA), and/or the like. More particularly, the invention pertains to a music player that is capable of controlling the speed of the music so as to affect the mood and behavior of the user during an activity such as exercise. By way of example, the speed of the music can be controlled to match the pace of the activity (synching the speed of the music to the activity of the user) or alternatively it can be controlled to drive the pace of the activity (increasing or decreasing the speed of the music to encourage a faster or slower pace).

One aspect of the invention relates to adjusting the tempo (or some other attribute) of music being outputted from a music player. By way of example, a song's tempo may be increased or decreased before or during playing. This is typically accomplished in real time (on the fly) in the music player. Another aspect of the invention relates to selecting music for outputting based on tempo (or some other attribute). For example, the music player may play songs having a particular tempo. Yet another aspect of the invention relates to both selecting music based on tempo and adjusting the tempo of the music.

These and other embodiments of the invention are discussed below with reference to FIGS. 1-23. However, those skilled in the art will readily appreciate that the detailed description given herein with respect to these figures is for explanatory purposes as the invention extends beyond these limited embodiments.

FIG. 1 is a simplified block diagram of a music player 10, in accordance with one embodiment of the present invention. The music player 10 includes a music manager 12 and a music store 14, both of which can be embodied as software or hardware or a combination of software and hardware. The music manager 12 controls the audio output of music files 16 stored in the music store 14. During operation, for example, the music manager 12 selects an audio track 18 from the music files 16 and outputs the audio track 18 in the form of an audio track.

In accordance with one embodiment, the music manager 12 is configured to select audio tracks 18 with particular characteristics and/or adjust characteristics of the audio tracks 18 to meet a particular need. In so doing, the music can be more closely matched to a user's mood and circumstances, and in some cases drive the mood and circumstances of the user. For example, the music manager 12 can select an audio track or adjust the characteristics of the audio track to match the behavior of the user, and/or it can select an audio track or adjust the characteristics of the audio track to encourage or drive the behavior of the user.

In one implementation, the music manager 12 is configured to adjust the tempo of an audio track or an audio track (as it is being outputted). This may be accomplished via a user selection or some external event. In the case of user selection, the user may set a desired tempo, and thereafter the media manager 12 may adjust the tempo of the audio tracks to match the desired tempo. In the case of events, the media manager may monitor an event and adjust the tempo of the audio track 18 based on the tempo of the event. In either case, the tempo may be adjusted incrementally or continuously (real time). When incrementally, the media manager 12 may sample the user selection or event at various times, and therefore only adjust the tempo at various times. When continuously, the media manager 12 continuously samples the user selection or event while the audio track 18 is being output, and simultaneously adjusts the tempo of the audio output with the tempo of the user selection or event as it changes.

The user selection may be performed in a variety of ways. In one example, the user selection is made through a GUI and a button or wheel that operates a slider bar on the GUI. The desired tempo changes as the slider bar is moved to various positions. The user can therefore select a desired tempo by simply moving the slider bar to a position associated with the desired tempo. Once a tempo is set, the music manager 12 can adjust the tempo of the audio track 18 accordingly. For example, if the user selects 120 beats per minute, and the audio track has a tempo of 140 beats per minute, then the music manager 12 can decrease the tempo of the audio track 18 from 140 bpm to 120 bpm thereby matching the tempo of the audio track with the selected tempo.

The events, which are typically monitored by the music manager 12, may be widely varied. In one example, the user events are associated with a body metric such as body motion, heart rate, respiratory rate, temperature, and the like. In most cases, these types of events are measured via sensors that send signals to the music manager 12 that are proportional to the tempo of the user event. For example, when the user event is body motion, and more particularly jogging, the sensors may send a signal indicative of the number of steps per minute, which can then be translated by the music manager 12 to beats per minute (bpm). For example, each step may represent one beat. The music manager after determining the tempo (bpm) of the user event can adjust the tempo of the audio track accordingly. For example, if the audio track has a tempo of 120 beats per minute, and the user event has a tempo of 140 beats per minute, then the music manager 12 can increase the tempo of the audio track from 120 bpm to 140 bpm thereby matching the tempo of the audio track with the tempo of the user event. Alternatively, the sensor itself may translate the step/m to beat/m.

In another implementation, the media manager 12 is configured to select audio tracks having tempos that closely match a desired tempo. The desired tempo may be based on a user selection or on some user event such as a body metric. For example, the user may set a desired tempo, and thereafter the media manager 12 may browse through all the music files 16 stored in the music store 14 looking for audio tracks 18 with similar tempos. Alternatively, the media manager 12 may monitor a user event, and thereafter the media manager 12 may browse through all the music files 16 stored in the music store 14 looking for audio tracks 18 with tempos similar to the user event. In either case, once matches are made, the media manager 12 outputs only those audio tracks, which have tempos that closely match the desired tempo.

In some cases, the music files 16 may contain multiple versions of the same audio track 18. Each version has a different tempo and therefore more audio tracks 18 may be made available for outputting. By way of example, the music files 16 may contain the original version 18A as well as one or more increased tempo versions 18B, and one or more decreased tempo versions 18C. The different versions may be part of the original music file, or they may be created when the music file is downloaded either to a host device that serves the music player 10 or to the music player 10 itself. Furthermore, in order to make it easier on the music manager 12 (save time and processing power), each audio track 18 may include a tag 20 that indicates the tempo of the audio track 18. The tag 20 may be part of the original music file, or it may be created when the music file is acquired (e.g., downloaded). By providing tags 20, the music manager 12 does not have to determine the tempo of each audio track 18 on its own. It simply has to select the audio tracks 16 with the desired tempo by looking at the tags 20. The tags and formats may be associated with metadata.

Figure 2A:
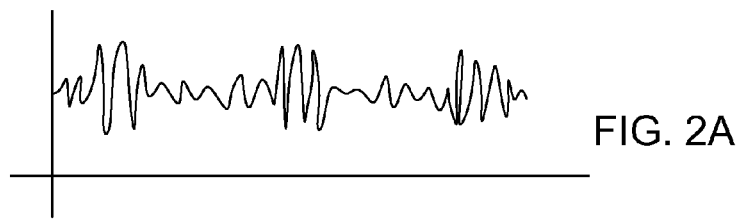
FIG. 2A is an illustration of an audio file signal, in accordance with one embodiment of the present invention.
Figure 2B:
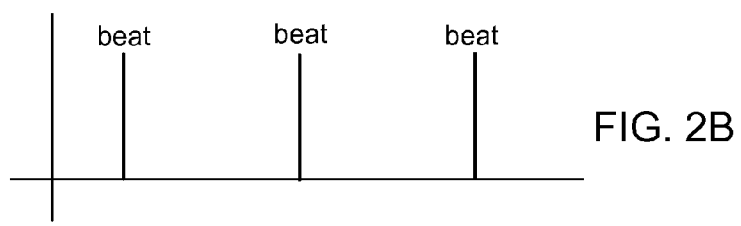
FIG. 2B is an illustration of a tag with beats annotated, in accordance with one embodiment of the present invention.

The tag may be a simple number such as 120 bpm or it may be based on the score that has the beats annotated. FIG. 2A is an example of an audio output signal, and FIG. 2B is an example of a preprocessed tag with the beats annotated for the audio output signal.

In yet another implementation, the music manager 12 is configured to both select audio tracks 18 having tempos that closely match a desired tempo, and to adjust the tempo of the audio track as it is being outputted. This is a combination of the two embodiments mentioned above. This particular embodiment may be used to reduce the processing power typically required to adjust the tempo of the audio track 18 at the music player 10. Because the tempo of the audio track has already been pre-selected to closely match the desired tempo, only small adjustments need to be made to more closely match the tempo of the audio track with the desired tempo. For example, if the desired tempo is 120 bpm, the music manager may select audio tracks having tags that indicate between about 115 bpm and about 125 bpm, and thereafter the music manager may adjust the audio track to bring it to 120 bpm.

Although the embodiments described above are primarily directed at "tempo matching" it should be noted that this is not a limitation and that the music manager may also be configured to drive events based on the tempo. For example, the music manager can select or adjust the tempo of music to illicit a change in a user event such as a body metric (e.g., the music manger can slow the tempo, thereby causing the user to slow their pace or the music manger can speed up the tempo, thereby causing the user to speed up their pace).

Figure 3:
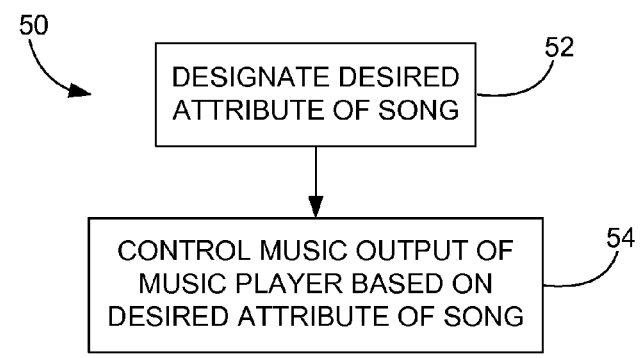
FIG. 3 is a music method performed on a music player, in accordance with one embodiment of the present invention.

FIG. 3 is a music method 50 performed on a music player, in accordance with one embodiment of the present invention. The method generally includes blocks 52 and 54. In block 52, an attribute of a song is designated. The attribute may for example correspond to tempo, rhythm, pitch, and the like. The designation may be accomplished by a user selection, i.e., a user selects the attribute and its desired value. The attribute is typically fixed once it is selected, i.e., it doesn't change until a user selects another attribute or another value. The designation may also be accomplished by monitoring an event such as a media player event, a user event, or the like. In this case, the attribute may be fixed or it may vary over time.

In block 54, the music output of the media player is controlled based on the designated attribute of the song. The music can be controlled in a variety of ways. In some cases, the actual attribute of the song is adjusted based on the designated attribute. For example, the actual attribute may be increased or decreased to match the designated attribute. In other cases, the songs that are selected for playing are based on the designated attribute. For example, only those songs with an actual attribute that matches the designated attribute may be played.

Figure 4:
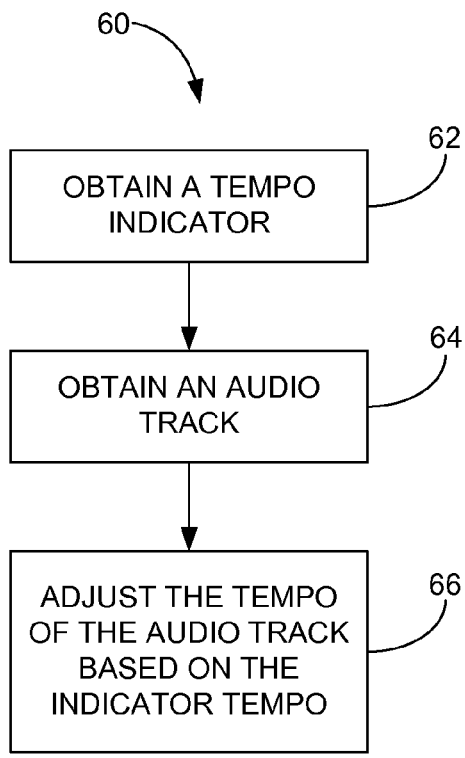
FIG. 4 is a music method performed on a music player, in accordance with one embodiment of the present invention.

FIG. 4 is a music method 60 performed on a music player, in accordance with one embodiment of the present invention. The method begins at block 62 where a tempo indicator is obtained. The tempo indication may be generated by a user selection or by monitoring some event. Once a tempo indicator is obtained, the method proceeds to block 64 where an audio track is obtained. For example, once an audio track is selected, the media player begins playing the audio track so that is can be transmitted to a speaker or headset. The method also includes block 66, which can occur before or during the playing (block 64). In block 66, the tempo of the audio track is adjusted based on the tempo indicator. In some cases, the tempo of the audio track is adjusted to match the tempo indicator, and in other cases, the tempo of the audio track is adjusted to effect a change, but not necessarily to match the two tempos. That is, the tempo indicator may be used to drive the tempo up and down in conjunction with some rules. For example, the tempo of the music may be a multiple or divisor of the user's pace ($\frac{2}{3}$x, $\frac{3}{4}$x, 2x, 3x, etc.).

Figure 5:
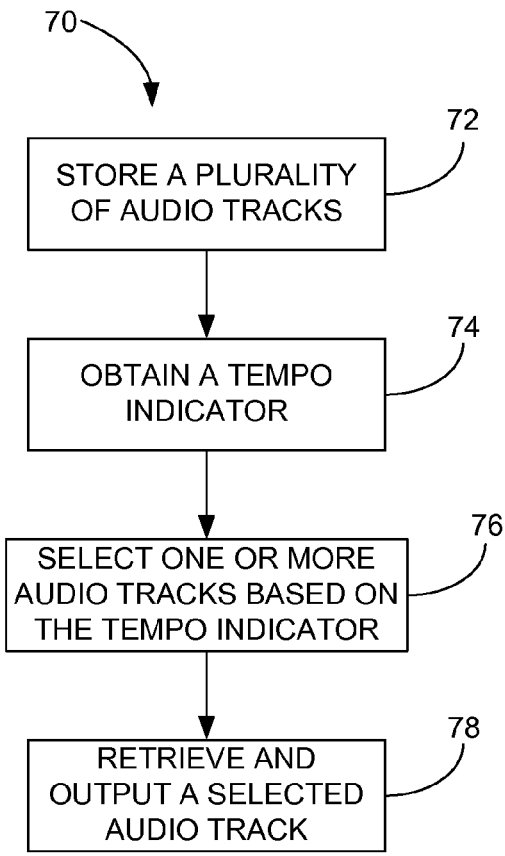
FIG. 5 is a music method performed on a music player, in accordance with one embodiment of the present invention.

FIG. 5 is a music method 70 performed on a music player, in accordance with one embodiment of the present invention. The method begins at block 72 where a plurality of songs, each of which has a tempo, are stored. The songs may for example be stored in memory. Thereafter in block 74, a tempo indicator is obtained. This block is similar to block 64 described above. Following block 74, the method proceeds to block 76 where one or more songs are selected from storage based on the tempo indicator. In some cases, the tempo of the song is selected to match to the tempo indicator, and in other cases, the tempo of the song is selected to effect a change, but not necessarily to match the two tempos. For example, the tempo indicator may be used to drive the tempo of the next song up and down in conjunction with some rules. Thereafter, in block 78, a least one of the selected songs is retrieved from storage and outputted.

In FIGS. 4 and 5, the step of obtaining the tempo of a user event such as a body metric may include generating a signal indicative of a user event and extracting tempo information from the user event. By way of example, if the user event is body motion, an accelerometer may be used to generate an acceleration signal indicative of the user's acceleration, and a controller of some sort may be used to extract the tempo of the user's motion from the acceleration signal. During extraction, one or more conversion or filtering steps can be performed in order to transform the user event signal into a tempo indication.

Figure 6:
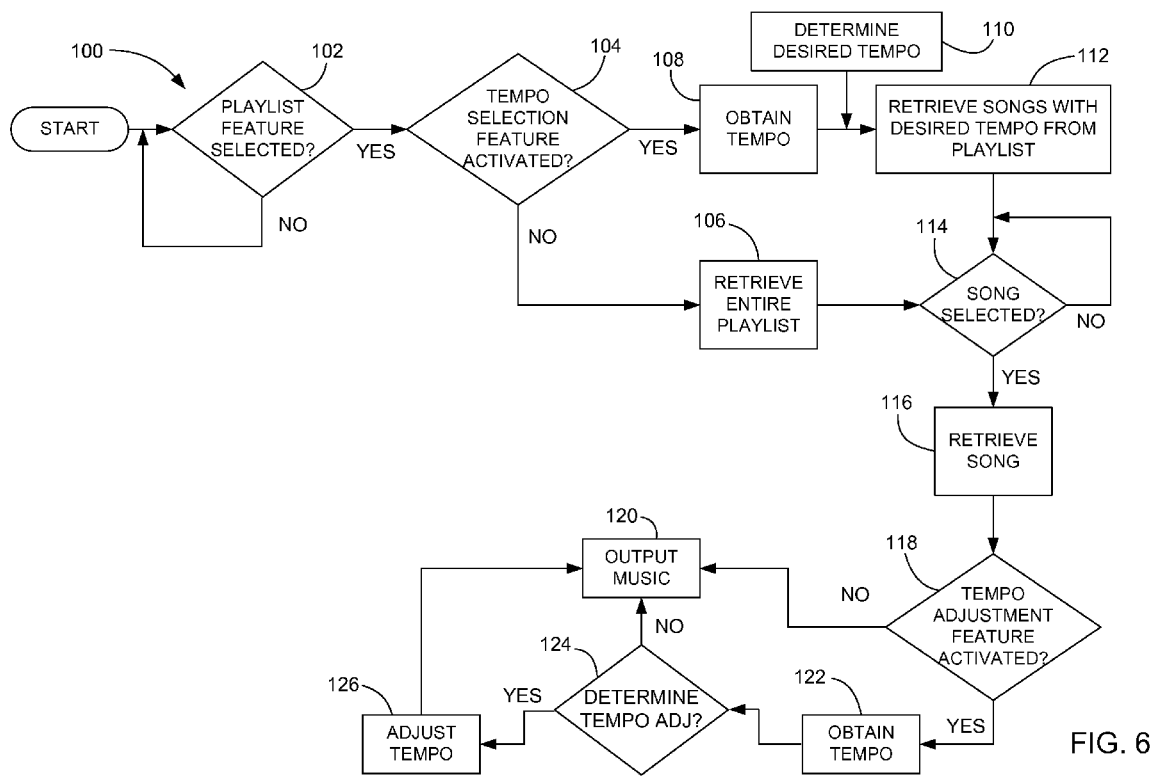
FIG. 6 is a music method performed on a music player, in accordance with one embodiment of the present invention.

FIG. 6 is a music method 100 performed on a music player, in accordance with one embodiment of the present invention. The method begins at block 102 where a determination is made as to whether or not a playlist feature is selected. A playlist is a plurality of songs that are grouped together. They may for example be grouped according to music genre, user ratings, most played, recently played, etc. The playlist is typically selected via a user interface that includes a display and an input device. If the playlist feature is not selected, the method waits.

If the playlist feature is selected, then the method proceeds to block 104 where a determination is made as to whether or not a tempo selection feature is active. If it is not active, the method proceeds to block 106 where the entire playlist is retrieved. If it is active, the method proceeds to block 108 where a tempo indicator is obtained. This may be accomplished via user selection, or monitoring an event and extracting tempo information from the event. If the tempo indicator is extracted from an event, the method may proceed to block 110 where the desired tempo is determined from the tempo indication. For example, the tempo indicator can be compared to a set of rules to calculate the desired tempo. In some cases the desired tempo is the same as the tempo indicator and in other cases the desired tempo is different. In the later case for example the rules may state that the tempo indicator is to low and thus the desired tempo should be increased. This may be done to drive the pace of the user. Following either blocks 108 or 110, the method proceeds to block 112 where songs from the playlist having the desired tempo are retrieved. In one embodiment, the retrieved songs are those having a tempo not substantially different than the desired tempo.

Following blocks 106 or 112, the method proceeds to block 114 where a determination is made as to whether or not a song is selected from the playlist (the entire playlist if the flow passed through block 106 and a modified playlist if the flow passed through block 110). This can be accomplished a variety of ways. For example, the user may manually select one song at a time or the user may select the first song and thereafter the songs may be selected automatically one after the other in some predetermined manner. Alternatively, the user can select a shuffle feature that randomly selects songs from the playlist. Once the song(s) is selected, the method proceeds to block 116 where the song is retrieved. Following block 116, the method proceeds to block 118 where a determination is made as to whether or not a tempo adjustment feature is active. If it is not active, the method proceeds to block 120 where the music is outputted. If the tempo adjustment feature is active, the method proceeds to block 122 where the tempo indicator is obtained for the retrieved song. For example, the tempo indicator for the retrieved song can be determined by analysis of its audio file or by a tempo tag. Once the tempo indicator is obtained, the method proceeds to block 124 where a determination is made as to whether or not a tempo adjustment is needed. If not, the music is outputted in block 120. If so, the tempo of the music is adjusted in block 126 and thereafter the modified music is outputted in block 120.

Figure 7:
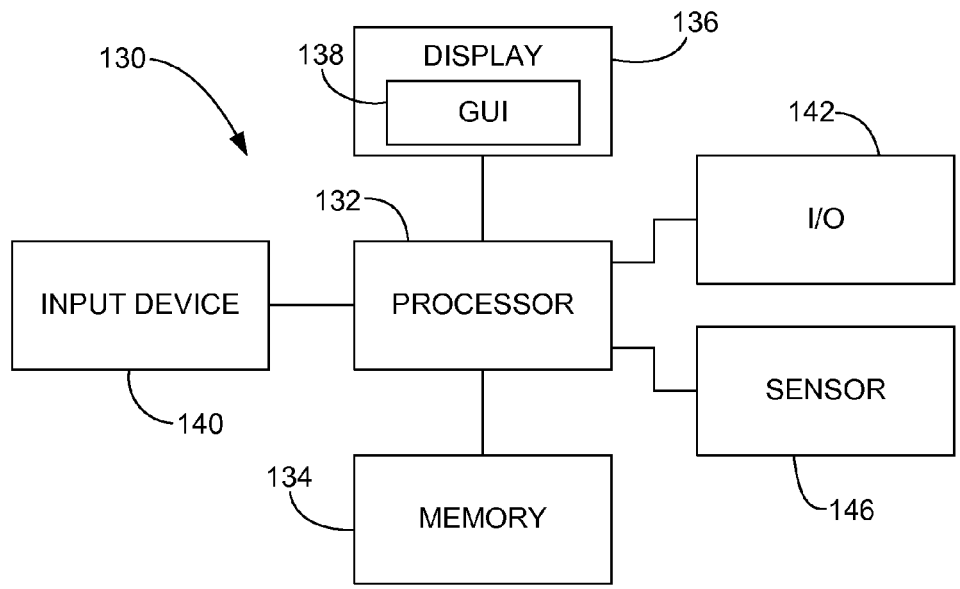
FIG. 7 is a block diagram of a music player system, in accordance with another embodiment of the present invention.

FIG. 7 is a block diagram of a music player system 130, in accordance with another embodiment of the present invention. As shown, the music player 130 includes a processor 132 configured to execute instructions and to carry out operations associated with the music player 130. For example, using instructions retrieved for example from memory, the processor 132 may control the reception and manipulation of input and output data between components of the music player system 130. The processor 132 can be implemented on a single-chip, multiple chips or multiple electrical components. For example, various architectures can be used for the processor 132, including dedicated or embedded processor, single purpose processor, controller, DSP, ASIC, and so forth.

In most cases, the processor 132 together with an operating system operates to execute computer code and produce and use data. The operating system, other computer code and data may reside within a memory block 134 that is operatively coupled to the processor 132. Memory block 134 generally provides a place to store computer code and data that are used by the music player system 130. By way of example, the memory block 134 may include Read-Only Memory (ROM), Random-Access Memory (RAM), hard disk drive and/or the like.

The music player system 130 also includes a display device 136 that is operatively coupled to the processor 132. The display device 136 may be a liquid crystal display (LCD) or a display implemented with electronic inks. The display device 136 is generally configured to display a graphical user interface (GUI) 138 that provides an easy to use interface between a user of the system 130 and the operating system or application running thereon. Generally speaking, the GUI 138 represents, programs, files and operational options with graphical images. The graphical images may include windows, fields, dialog boxes, menus, icons, buttons, cursors, scroll bars, etc. The GUI 138 can additionally or alternatively display information, such as non-interactive text and graphics, for the user on the display device 136.

The music player system 130 also includes an input device 140 that is operatively coupled to the processor 132. The input device 140 is configured to transfer data from the outside world into the music player system 130. The input device 140 may for example be used to perform tracking and to make selections with respect to the GUI 138 on the display 136. The input device 140 may also be used to issue commands in the music player system 130. By way of example, the input device may be selected from keys, buttons, wheels, knobs, joysticks, touch pads, touch screens, and/or the like.

The music player system 130 also includes input/output circuitry 142 that is operatively coupled to the processor 132. The input/output circuitry 142 allows connections to one or more I/O devices 144 that can be coupled to the music player system 130. The processor 132 generally operates by exchanging data between the music player system 130 and I/O devices 144 that desire to communicate with the music player system 130. The I/O devices 144 may be connected through wired connections or through wireless connections. In the case of a music player, the I/O circuitry 142 may include an audio jack so that speakers or earphones can be plugged into the music player system 130, and a data port so that music can be transferred between the music player system 130 and a host.

The music player system 130 also includes a sensor 146 that is operatively coupled to the processor 132. Like the input device 140, the sensor 146 is configured to transfer data from the outside world into the music player system 130. The sensor 146 generally includes capabilities for measuring some event. The sensor may for example be used to monitor a user's body metrics such as body motion or heart rate. The sensor 146 may be located internal or external relative to the housing of the music player. If internal, it is typically fixed within the housing. If external, it may be fixed to the outside of the housing or it may be located peripherally away from the housing (e.g., peripheral device). In most cases, the sensor is positioned inside the media player housing in order to decrease the wires and cords that often get in the way of a user when the user tries to exercise or move around.

It should be noted, however, there are times when this isn't practical as for example when the event cannot be easily measured from an onboard sensor. In the case of body metric, the sensor 146 may be attached to some mechanism for securing the sensor 146 to a user's body so that a body metric can be measured. For example, the sensor 146 may be integrated with a band, belt, or some other article of clothing. The sensor 146 may also be integrated into a piece of exercise equipment as for example treadmills, stair climbers, rowing machines, punching bags, and the like. The data measured by the external sensor 146 may be transferred through a wired or wireless connections. For example, a cable may be used to connect the sensor 146 to the music player system 130 through the I/O circuitry or a wireless link such as Bluetooth, 802.11. UWB (ultra wide band), IR, and the like may be used Like an internal sensor, a wireless link prevents the use of cables and cords.

The sensor 146 may be widely varied. The sensor 146 may correspond to pressure switches, proximity sensors, accelerometers, optical sensors and the like. In the case of body motion, accelerometers that measure acceleration work particularly well. The accelerometer can be a single, biaxial or triaxial accelerometer depending on the needs of the system. The accelerometer can process the raw data and then send the processed data to the processor or alternatively, the raw data can be sent to the processor for processing the raw data. In the first case, the accelerometer may be embedded in a chip that has built in amplifiers and analog to digital converters resulting in a serial digital output signal that can be connected directly to the processor.

In accordance with one embodiment, the media player is configured to control the tempo of the music being outputted from the media player based on the signal from the sensor. In the case of a body metric such as body motion or heartbeat, the sensor measures a body metric and converts the body metric into a signal indicative of the body metric. The signal is sent to the processor that analyzes the signal and extracts tempo information from the body metric signal. The processor then refers to a set of rules that tell the processor how to affect the music being outputted based on the tempo information. The rules may for example be stored in the memory block. After consulting the rules, the processor may select a particular song for outputting based on the tempo information. (i.e., select a song that has a tempo that matches the tempo information, select a song that has a tempo greater than the tempo information, select a song that has a tempo that is lower than the tempo information). Additionally or alternatively, the processor may modify the song itself based on the tempo information (i.e., increase or decrease the tempo of the song in accordance with the tempo of the body metric).

In one embodiment, the rules are embodied in a tempo control program for controlling the tempo of the music to be outputted. The tempo program may be accessed by a user through a tempo control menu, which may be viewed on the display device 170 as part of a GUI interface. The tempo control menu may include various options. In fact, the tempo control menu may serve as a control panel for reviewing and/or customizing the tempo control settings, i.e., the user may quickly and conveniently review the tempo control settings and make changes thereto. Once changed, the modified tempo control settings will be automatically saved and thereby employed to handle future tempo processing.

The tempo control program may include a beat synch module that is configured to modify the outgoing audio. For example, it is capable of adjusting the tempo of the music being outputted from the music player system. Once a song has been selected, the audio associated with the song is played so that a user can listen to the song. If the beat synch module is activated, it will adjust the tempo of the playing audio based on the tempo obtained from the sensor. The adjustment may be made using an algorithm capable of adjusting the tempo in a non-trivial manner. The algorithm may for example be associated with phase vocoding or SFFT processing. Phase vocoding is a complex signal processing technique that includes elements of LPC (linear predictive coding). It uses continuous and overlapping Fourier transforms of a sound for several related objectives ranging from resynthesis, and timbral interpolation from one sound to another, to time stretching (altering the tempo without affecting the pitch) and pitch shifting (transposition of a sound without altering the tempo). Traktor DJ studio manufactured by Native Instruments of Germany is one example of a program that uses phase vocoding.

Figure 8:
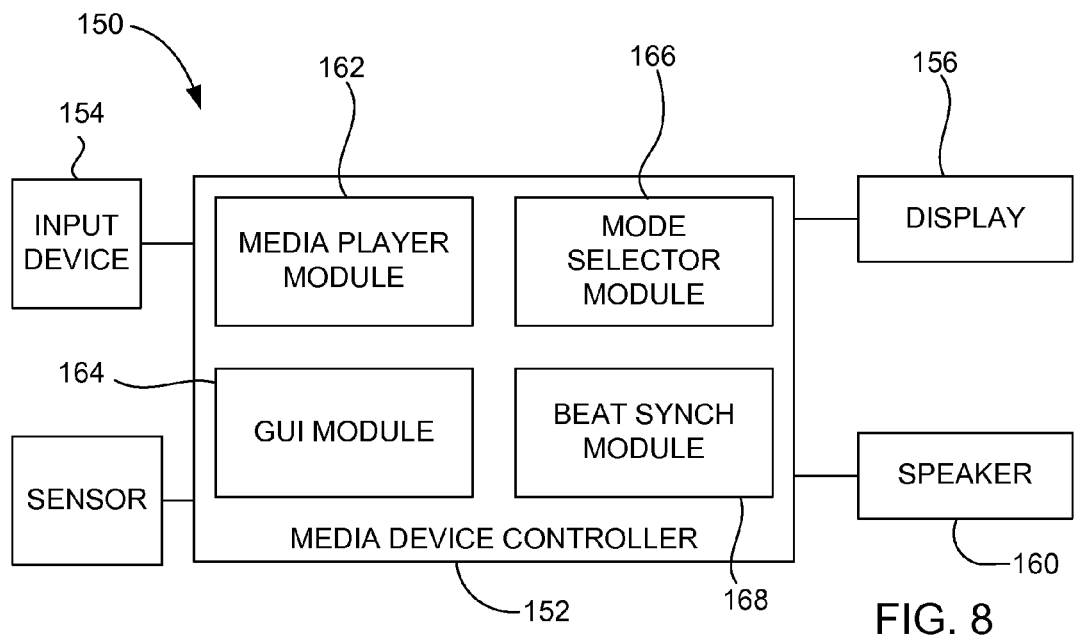
FIG. 8 is a block diagram of a media player system, in accordance with one embodiment of the present invention.

FIG. 8 is a block diagram of a media player system 150, in accordance with one embodiment of the present invention. The media player system 150 generally includes a media device controller 152 that directs inputs and outputs between an input device 154, a display 156, a sensor 158 and a speaker 160. By way of example, the input device 154 may be a touch pad or button, the display 156 may be an LCD, the sensor 158 may be an accelerometer, and the speaker 160 may be a headphone or speaker set.

The media device controller 152 includes several modules, which may be hardware, software, or a combination of both hardware and software. As shown, the media device controller 152 includes at least a media player module 162, a GUI module 164, a mode selector module 166 and a beat synch module 168. The modules may work individually or together with other modules in order to process media information. The media player module 162 is primarily configured to run the media aspects of the media player system 100. That is, the media player module 162 controls the overall activity of the media player system 150. For example, the media player module 162 may include capabilities for inputting and outputting audio information. The GUI module 164 controls the information presented on the display 156. The GUI module 164 may for example present a graphical user interface in the form of text or graphics on the display 156. The mode selector module 166 controls which mode the media player 150 is in. For example, in the case of tempo, whether the media player 150 is in a manual, automatic or training mode. The beat synch module 168 helps control the tempo of the music output. That is, the beat synch module 168 along with the media player module select a song with the desired tempo or it can adjust the tempo of the music before or during the time when it's played. By way of example, the beat synch module may utilize phase vocoding techniques in order to adjust the tempo (or other attribute of the music such as pitch). The media player module 162 may include a set of instructions that tell the beat synch module 168 what to do with the music based on what mode the mode selector 166 module is in. By way of example, the media player module 162 may instruct the beat synch module to increase or decrease the tempo of the music.

During one particular operation of the system, the GUI module 164 (for example after referring to the mode selector module 166) presents a list of tempo modes on the display 156. Using the input device 154, the user selects one of the tempo modes from the list of tempo modes. By way of example, the user may use a touch pad to move a selector bar though the list of tempo modes and a button to select the desired tempo mode, i.e., the mode around which the selector bar is positioned. The mode selector module 166 receives the selection signal, and changes the tempo mode based on the selection signal. Once the tempo mode has been set, the selected tempo mode will be employed to handle future music events. The tempo modes may be widely varied. If a manual mode is selected, the beat synch module will adjust the tempo of the music based on a user entry. If an automatic mode is selected, the beat synch module will adjust the music based on some event such as a body metric measured by the sensor 158. If a training mode is selected, the beat synch module will adjust the music to help drive the user's work out.

Figure 9:
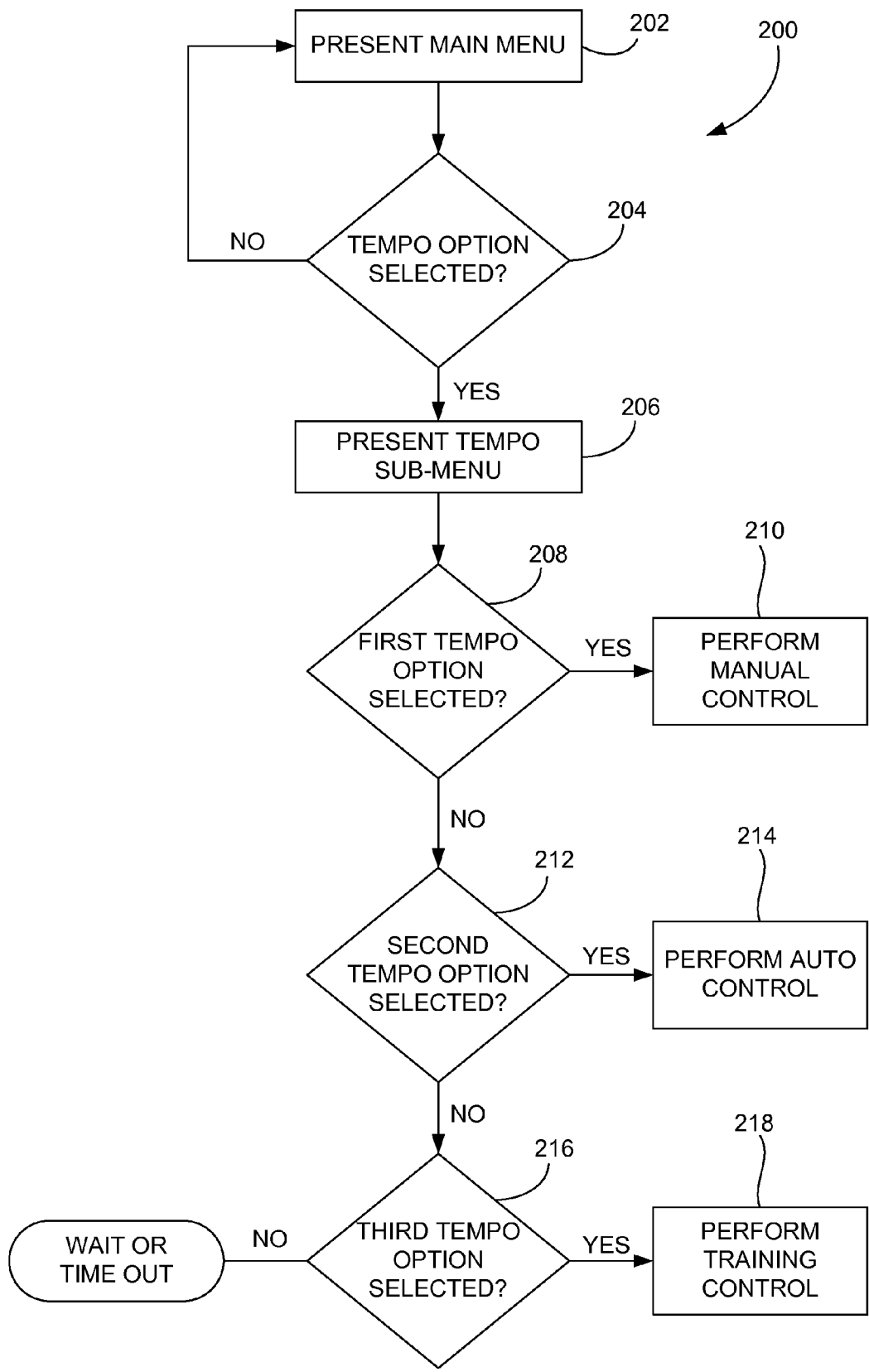
FIG. 9 is an operational method, in accordance with one embodiment of the present invention.

FIG. 9 is an operational method 200, in accordance with one embodiment of the present invention. The operational method 200 may for example be performed on a music player such as any of those described herein. The method 200 generally begins at block 202 where a main menu is presented to a user on a display. See for example FIG. 10A, which shows the main menu 250 presented on the display 248. The main menu 250 generally includes several options 252 associated with operating the music player. By way of example, the main menu 250 may include options 252 such as playlists, browse, extras, settings, shuffle, backlight, tempo, etc. In most cases, each of the options 252 includes its own sub menu of sub options, which are associated with the main option.

Figure 10A:
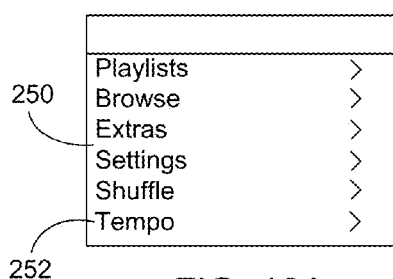
FIGS. 10A-10I show various screen shots of a computing device, in accordance with one embodiment of the present invention.
Figure 10B:
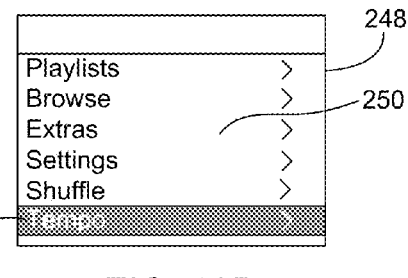
Figure 10C:
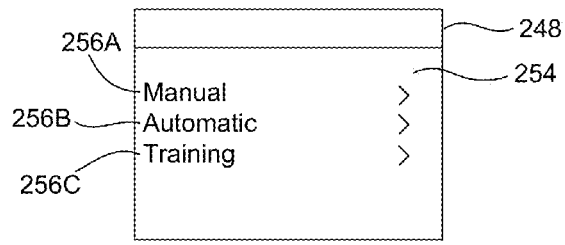

Following block 202, the method proceeds to block 204 where a determination is made as to whether the tempo option was selected. If not, the method proceeds back to block 202. If so (as shown in FIG. 10B), the method proceeds to block 206 where the tempo sub menu is presented to the user on the display. By way of example, see FIG. 10C which shows the tempo sub menu 254 presented on the display 248. The tempo sub menu 254 generally includes one or more tempo options 256, which represent different modes of tempo control. In the illustrated embodiment, the sub menu 254 includes at least a first option 256A and a second option 256B. Each of these options 256 is configured to initiate a different control operation when selected. For example, the first option may initiate manual tempo control, and the second option may initiate automatic tempo control. Alternatively or additionally, a third option 256C, may be included that initiates training tempo control.

Figure 10D:
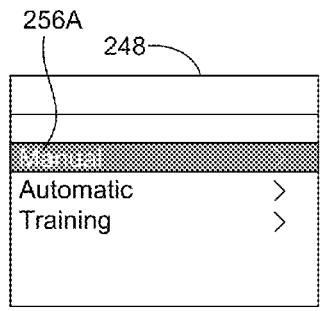
Figure 10F:
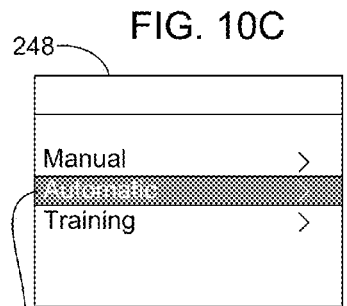
Figure 10H:
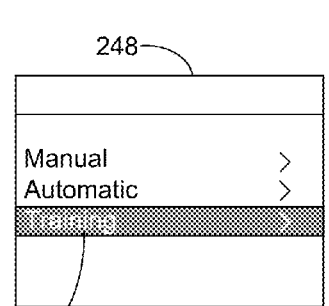
Figure 10E:
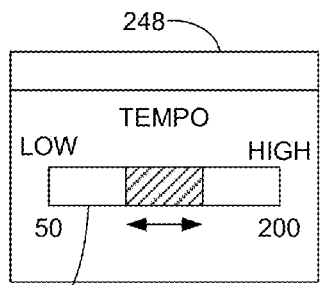

Following block 206, the method proceeds to block 208 where a determination is made as to whether the first option is selected. If it is selected (as shown in FIG. 10D), the method proceeds to block 210 where manual tempo control is performed. In manual tempo control, the user can manually enter a desired tempo. This can be accomplished through a user interface element such as slider bar 260 (as shown in FIG. 10E), through alphanumeric entry, by selecting from a list of tempos, or by selecting a multiple of the tempo (⅔×, ¾×, 2×, 3×, etc.). Although exact values are typically selected, in some cases it may be desirable to offer only a few values in order to simplify the operation of the device. In cases such as these, the user may only be presented with a few tempo options such as andante (which is a moderately slow tempo), allegro (which is a brisk and lively tempo), or allegretto (which is a quicker tempo than andante but not as fast as allegro). Accelerando (which is a gradually increasing tempo of music) or rubato (which is a flexible tempo, not strictly on the beat) may also be made available.

Figure 10G:
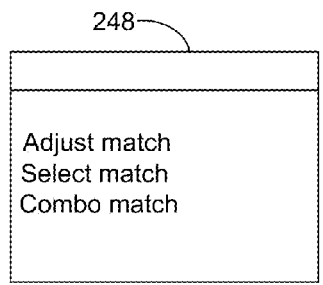

If the first option is not selected, the method proceeds to block 212 where a determination is made as to whether the second option is selected. If it is selected (as shown in FIG. 10F), the method proceeds to block 214 where the media player performs automatic tempo control. In automatic tempo control, the media player automatically controls the tempo based on some event. The event may for example be a user event that is measured by a sensor. By way of example, the sensor may be an accelerometer located within the media player. In cases such as this, the acceleration data can be used to determine the pace of the user when the media player is worn on the user. The pace can be converted to tempo, and this tempo value can be used to drive the tempo of the music being outputted (e.g., adjust the audio track, select a song with the desired tempo, etc.). As such, the tempo of the music can be matched to the pace of the user. For example, the tempo may be increased when the user's pace increases or it may be decreased when the user's pace decreases (or vice versa). Alternatively or additionally, the songs being outputted can be carefully selected to match the pace of the user. As shown in FIG. 10G, the user may be prompted with a submenu that allows a user to select tempo features such as "adjust match", "select match", or "combo."

If the first and second options are not selected, the method proceeds to block 212 where a determination is made as to whether the third option is selected. If it is selected (as shown in FIG. 10H), the method proceeds to block 214 where the media player is placed in a training mode. In the training mode, the tempo of the music is adjusted to help drive the user's workout. The tempo serves as the coach or trainer to the user. This can be accomplished before the workout or during the workout.

Figure 10I:
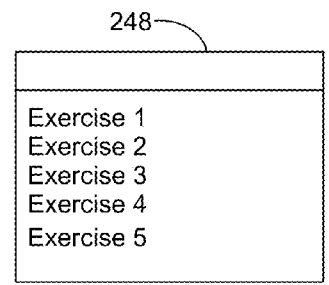
Figure 11A:
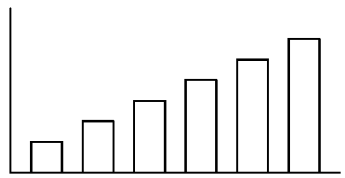
FIGS. 11A-11E show various work out programs, in accordance with one embodiment of the present invention.
Figure 11B:
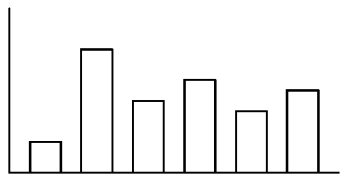
Figure 11C:
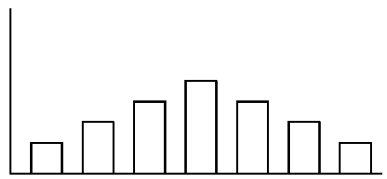
Figure 11D:
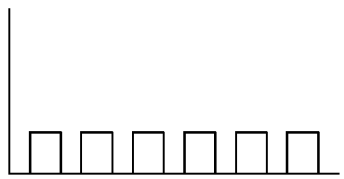
Figure 11E:
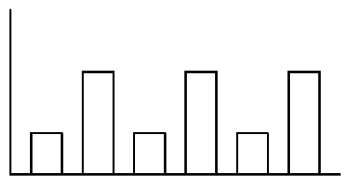

In one embodiment, the user may be presented with a list of exercise regimes (as shown in FIG. 10I), each or which has a different exercise profile associated with the pace desired by the user during their exercise sequence. Each exercise profile has a tempo profile associated therewith that matches the pace of the exercise profile. When the user selects an exercise profile and begins the workout, the tempo is adjusted according to the tempo profile and therefore the tempo can be used to help drive the pace of the user (either subconsciously or by the user recognizing that the tempo has increased or deceased). FIGS. 11A-11E are graphical illustrations of several exercise regimes, which show pace as a function of time. More particularly, FIG. 11A shows a hill work out, FIG. 11B shows a random workout, FIG. 11C shows a cardio workout, FIG. 11D shows a fat burn workout, FIG. 11E shows speed interval work out.

In another embodiment, the user may select pace threshold values instead of an exercise regime. In this embodiment, if the user falls below or above the pace thresholds the tempo is adjusted to help direct the user to increase or decrease their pace. By way of example, if the heart rate of the user goes above a set limit then the tempo of the music may reduced so as to encourage the user to slow their pace and therefore their heart rate or if the heart rate of the user goes below a set limit then the tempo of the music may be increased so as to encourage the user to increase their pace and therefore their heart rate.

Figure 12:
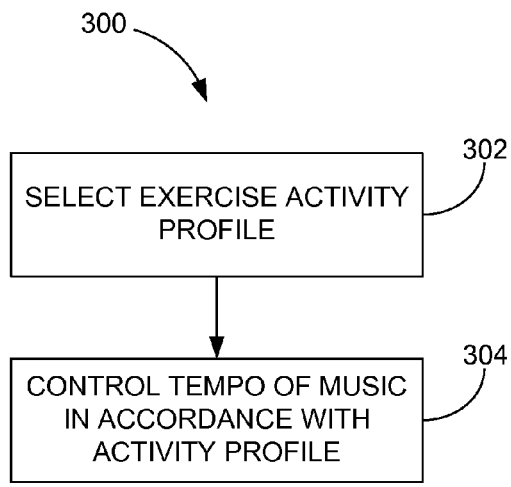
FIG. 12 is an operational method performed on a portable media device, in accordance with one embodiment of the present invention.

FIG. 12 is an operational method 300 performed on a portable media device, in accordance with one embodiment of the present invention. The method begins at block 302 where a user selects an exercise activity profile. Exercise activity profiles may for example those shown in FIGS. 11A-11E. Following block 302, the method proceeds to block 304 where the tempo of the music is controlled in accordance with the activity profile. For example, if the activity profile includes increasing levels of pace, the tempo of the song being played at the time may be selected or adjusted to increase with the increasing levels of pace of the activity profile. In so doing, the tempo can help the user maintain his pace in accordance with the activity profile. Alternatively or additionally, each activity profile may have a sequence of songs associated therewith. During the activity, the songs are played in some predetermined manner to drive the workout.

Figure 13:
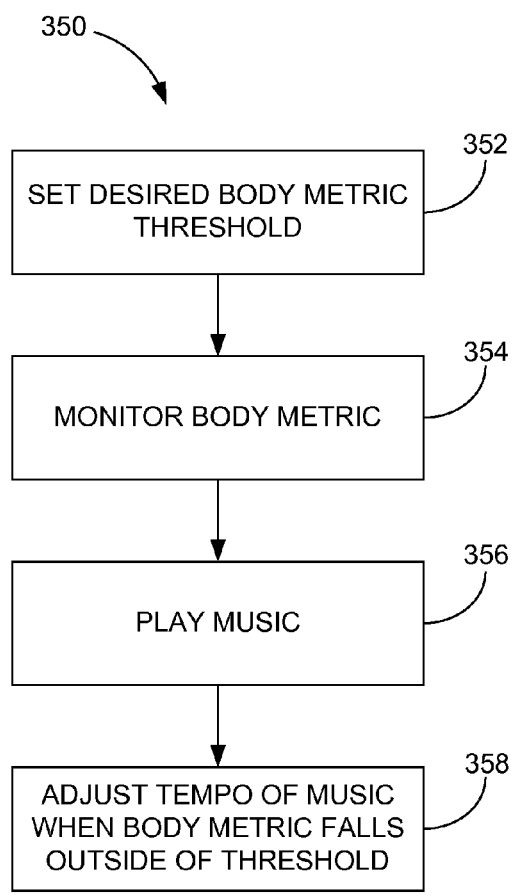
FIG. 13 is an operational method performed on a portable media device, in accordance with one embodiment of the present invention.

FIG. 13 is an operational method 350 performed on a portable media device, in accordance with one embodiment of the present invention. The method generally begins at block 352 where a desired body metric threshold is set. For example, upper and lower control limits of pace or heart rate may be entered. Following block 352, the method proceeds to block 354 where the body metric is monitored. For example, the user's pace may be monitored with an accelerometer and a users heart rate can be monitored with a heart rate sensor, which are used in well-known heart rate monitors. Following block 354, the method proceeds to block 356 where music is played on the media player. Following block 356, the method proceeds to block 358 where the tempo of the music is controlled when the body metric falls outside of the desired body metric threshold set by the user. For example, different songs may be played and/or the tempo of the current song being played may be adjusted.

To cite an example using the above technique. The user enters an upper heart rate as for example 160 and a lower heart rate as for example 120. Thereafter when the user is exercising and listening to music, the heart rate of the user is monitored. If the heart rate falls below the lower limit, the tempo of the song is increased either by selecting a new song with the appropriate tempo and/or by adjusting the currently played song. If the heart rate rises above the upper limit, the tempo of the song is decreased either by selecting a new song with the appropriate tempo and/or by adjusting the currently played song.

Figure 14:
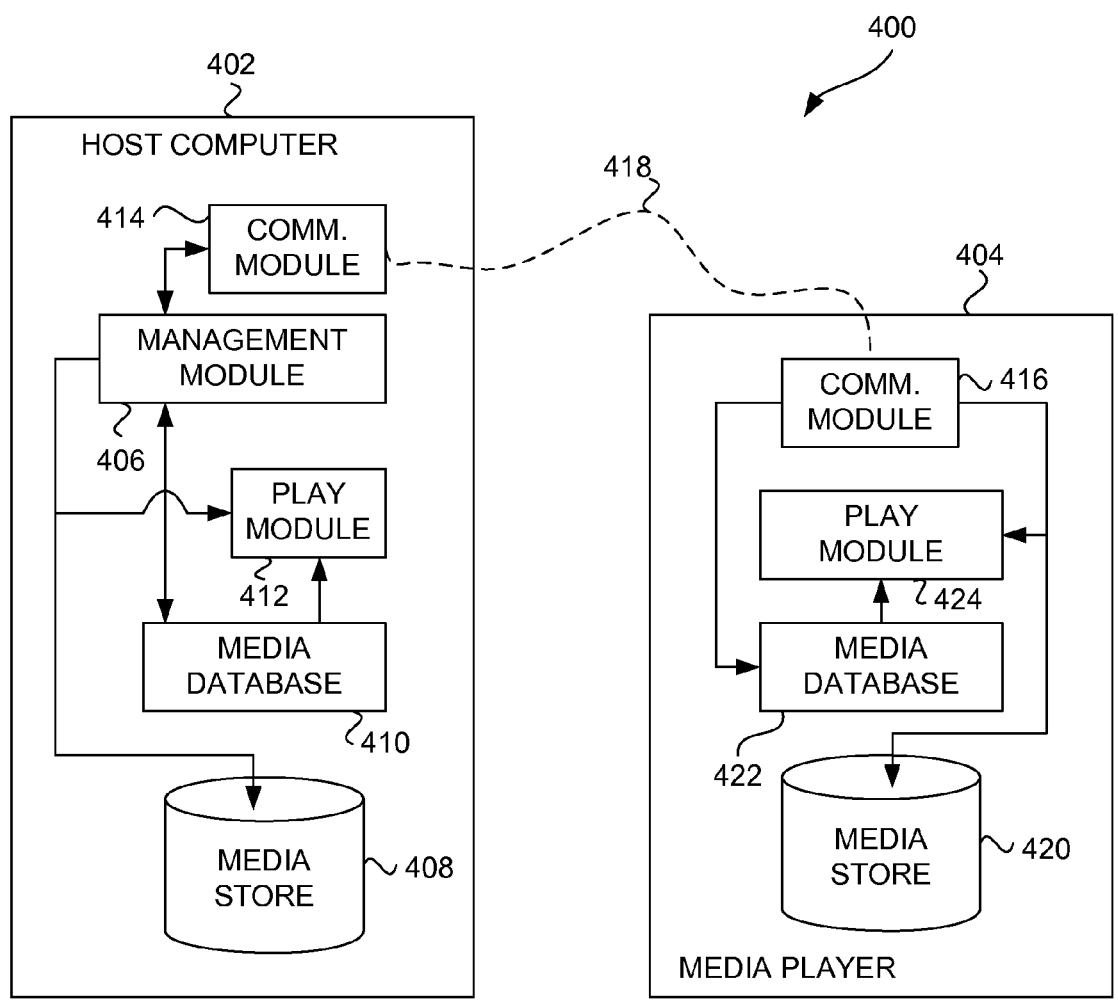
FIG. 14 is a block diagram of a media management system, in accordance with one embodiment of the present invention.

FIG. 14 is a block diagram of a media management system 400, in accordance with one embodiment of the present invention. The media management system 400 includes a host computer 402 and a media player 404. The host computer 402 is typically a personal computer. The host computer, among other conventional components, includes a management module 406, which is a software module. The management module 406 provides for centralized management of media items (and/or playlists) not only on the host computer 402 but also on the media player 404. More particularly, the management module 406 manages those media items stored in a media store 408 associated with the host computer 402. The management module 406 also interacts with a media database 410 to store media information associated with the media items stored in the media store 408.

The media information pertains to characteristics or attributes of the media items. For example, in the case of audio or audiovisual media, the media information can include one or more of: title, album, track, artist, composer and genre. These types of media information are specific to particular media items. In addition, the media information can pertain to quality characteristics of the media items. Examples of quality characteristics of media items can include one or more of: bit rate, sample rate, equalizer setting, and volume adjustment, start/stop and total time.

Still further, the host computer 402 includes a play module 412. The play module 412 is a software module that can be utilized to play certain media items stored in the media store 408. The play module 412 can also display (on a display screen) or otherwise utilize media information from the media database 410. Typically, the media information of interest corresponds to the media items to be played by the play module 412.

The host computer 402 also includes a communication module 414 that couples to a corresponding communication module 416 within the media player 404. A connection or link 418 removeably couples the communication modules 414 and 416. In one embodiment, the connection or link 418 is a cable that provides a data bus, such as a FIREWIRE™ bus or USB bus, which is well known in the art. In another embodiment, the connection or link 418 is a wireless channel or connection through a wireless network. Hence, depending on implementation, the communication modules 414 and 416 may communicate in a wired or wireless manner.

The media player 404 also includes a media store 420 that stores media items within the media player 404. The media items being stored to the media store 420 are typically received over the connection or link 418 from the host computer 402. More particularly, the management module 406 sends all or certain of those media items residing on the media store 408 over the connection or link 418 to the media store 420 within the media player 404. Additionally, the corresponding media information for the media items that is also delivered to the media player 404 from the host computer 402 can be stored in a media database 422. In this regard, certain media information from the media database 410 within the host computer 402 can be sent to the media database 422 within the media player 404 over the connection or link 418. Still further, playlists identifying certain of the media items can also be sent by the management module 406 over the connection or link 418 to the media store 420 or the media database 422 within the media player 404.

Furthermore, the media player 404 includes a play module 424 that couples to the media store 420 and the media database 422. The play module 424 is a software module that can be utilized to play certain media items stored in the media store 420. The play module 424 can also display (on a display screen) or otherwise utilize media information from the media database 422. Typically, the media information of interest corresponds to the media items to be played by the play module 424.

Hence, in one embodiment, the media player 404 has limited or no capability to manage media items on the media player 404. However, the management module 406 within the host computer 402 can indirectly manage the media items residing on the media player 404. For example, to "add" a media item to the media player 404, the management module 406 serves to identify the media item to be added to the media player 404 from the media store 408 and then causes the identified media item to be delivered to the media player 404. As another example, to "delete" a media item from the media player 404, the management module 406 serves to identify the media item to be deleted from the media store 408 and then causes the identified media item to be deleted from the media player 404. As still another example, if changes (i.e., alterations) to characteristics of a media item were made at the host computer 402 using the management module 406, then such characteristics can also be carried over to the corresponding media item on the media player 404. In one implementation, the additions, deletions and/or changes occur in a batch-like process during synchronization of the media items on the media player 404 with the media items on the host computer 402.

In another embodiment, the media player 404 has limited or no capability to manage playlists on the media player 404. However, the management module 406 within the host computer 402 through management of the playlists residing on the host computer can indirectly manage the playlists residing on the media player 404. In this regard, additions, deletions or changes to playlists can be performed on the host computer 402 and then by carried over to the media player 404 when delivered thereto.

Figure 15:
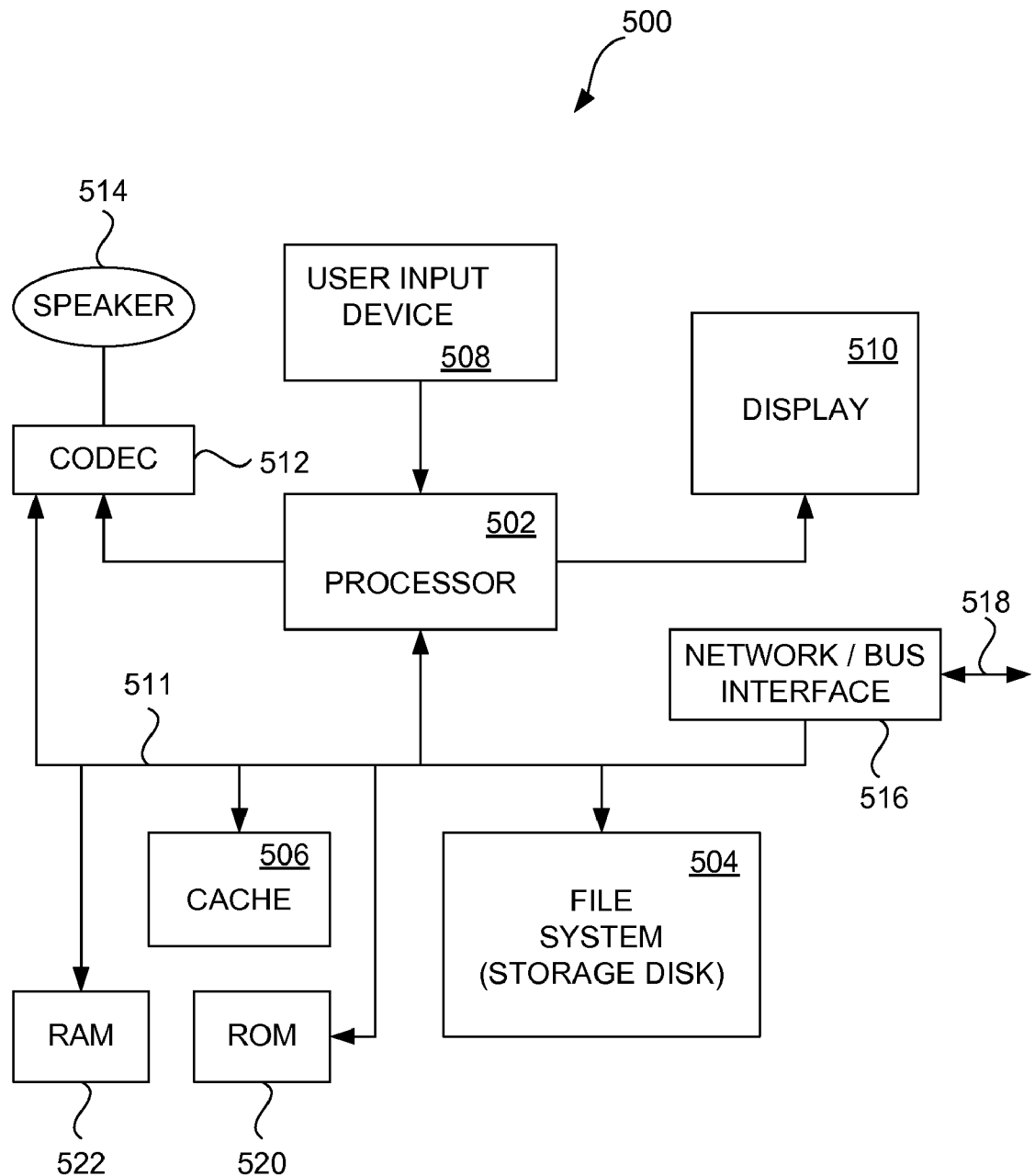
FIG. 15 is a block diagram of a media player, in accordance with one embodiment of the present invention.

FIG. 15 is a block diagram of a media player 500, in accordance with one embodiment of the present invention. The media player 500 includes a processor 502 that pertains to a microprocessor or controller for controlling the overall operation of the media player 500. The media player 500 stores media data pertaining to media items in a file system 504 and a cache 506. The file system 504 is, typically, a storage disk or a plurality of disks. The file system 504 typically provides high capacity storage capability for the media player 500. However, since the access time to the file system 504 is relatively slow, the media player 500 can also include a cache 506. The cache 506 is, for example, Random-Access Memory (RAM) provided by semiconductor memory. The relative access time to the cache 506 is substantially shorter than for the file system 504. However, the cache 506 does not have the large storage capacity of the file system 504. Further, the file system 504, when active, consumes more power than does the cache 506. The power consumption is often a concern when the media player 500 is a portable media player that is powered by a battery (not shown). The media player 500 also includes a RAM 520 and a Read-Only Memory (ROM) 522. The ROM 522 can store programs, utilities or processes to be executed in a non-volatile manner. The RAM 520 provides volatile data storage, such as for the cache 506.

The media player 500 also includes a user input device 508 that allows a user of the media player 500 to interact with the media player 500. For example, the user input device 508 can take a variety of forms, such as a button, keypad, dial, etc. Still further, the media player 500 includes a display 510 (screen display) that can be controlled by the processor 502 to display information to the user. A data bus 511 can facilitate data transfer between at least the file system 504, the cache 506, the processor 502, and the CODEC 512.

In one embodiment, the media player 500 serves to store a plurality of media items (e.g., songs) in the file system 504. When a user desires to have the media player play a particular media item, a list of available media items is displayed on the display 510. Then, using the user input device 508, a user can select one of the available media items. The processor 502, upon receiving a selection of a particular media item, supplies the media data (e.g., audio file) for the particular media item to a coder/decoder (CODEC) 1012. The CODEC 512 then produces analog output signals for a speaker 1014. The speaker 514 can be a speaker internal to the media player 500 or external to the media player 500. For example, headphones or earphones that connect to the media player 500 would be considered an external speaker.

The media player 500 also includes a network/bus interface 516 that couples to a data link 518. The data link 518 allows the media player 500 to couple to a host computer. The data link 518 can be provided over a wired connection or a wireless connection. In the case of a wireless connection, the network/bus interface 516 can include a wireless transceiver.

In another embodiment, a media player can be used with a docking station. The docking station can provide wireless communication capability (e.g., wireless transceiver) for the media player, such that the media player can communicate with a host device using the wireless communication capability when docked at the docking station. The docking station may or may not be itself portable.

The wireless network, connection or channel can be radio frequency based, so as to not require line-of-sight arrangement between sending and receiving devices. Hence, synchronization can be achieved while a media player remains in a bag, vehicle or other container.

In accordance with another embodiment, the present invention also relates to music transfer between portable media devices and their hosts. As mentioned above, media devices with tempo controlling functionality may require several different song versions. For example, media devices may require an original version of a song for normal listening pleasure as well as various "thumbnail" versions of the original for enhanced tempo effecting use.

One method for creating these various versions is to download the original song to the portable media device and then to convert the original song into the various versions on the portable media device when needed (either before or during outputting). This is sometimes referred to as processing data on the fly. While this may work well, it may have several drawbacks that make it less appealing to the user. For example, because reformatting a song (i.e., adjusting its tempo) is a process intensive task (especially on portable media devices that lack the horsepower of their larger hosts), portable media devices may operate slowly and consume more power.

In lieu of the above, the present invention provides a method where songs are preformatted on the host before or during the download thereto. When a song is identified for download various preformatted songs derived from the original are sent to the portable media device. The processing is performed on the host, which can handle these tasks more easily than the portable media player. The tasks may, for example, include adjusting tempo of the original in order to create new versions with different tempos. Once received by the portable media device, the original and preformatted songs are stored for later use. By storing these songs, the media device is relieved from having to perform any of the labor-intensive tasks associated with song formatting. As a result, the device operates faster and without repeated needs for recharging.

During media device use, a user may request that a song to be outputted. Instead of processing the original song as in the method described above, the device simply obtains the appropriate preformatted song from storage and outputs it to the user. The preformatted songs may include a high tempo, medium tempo and low tempo version.

Figure 16:
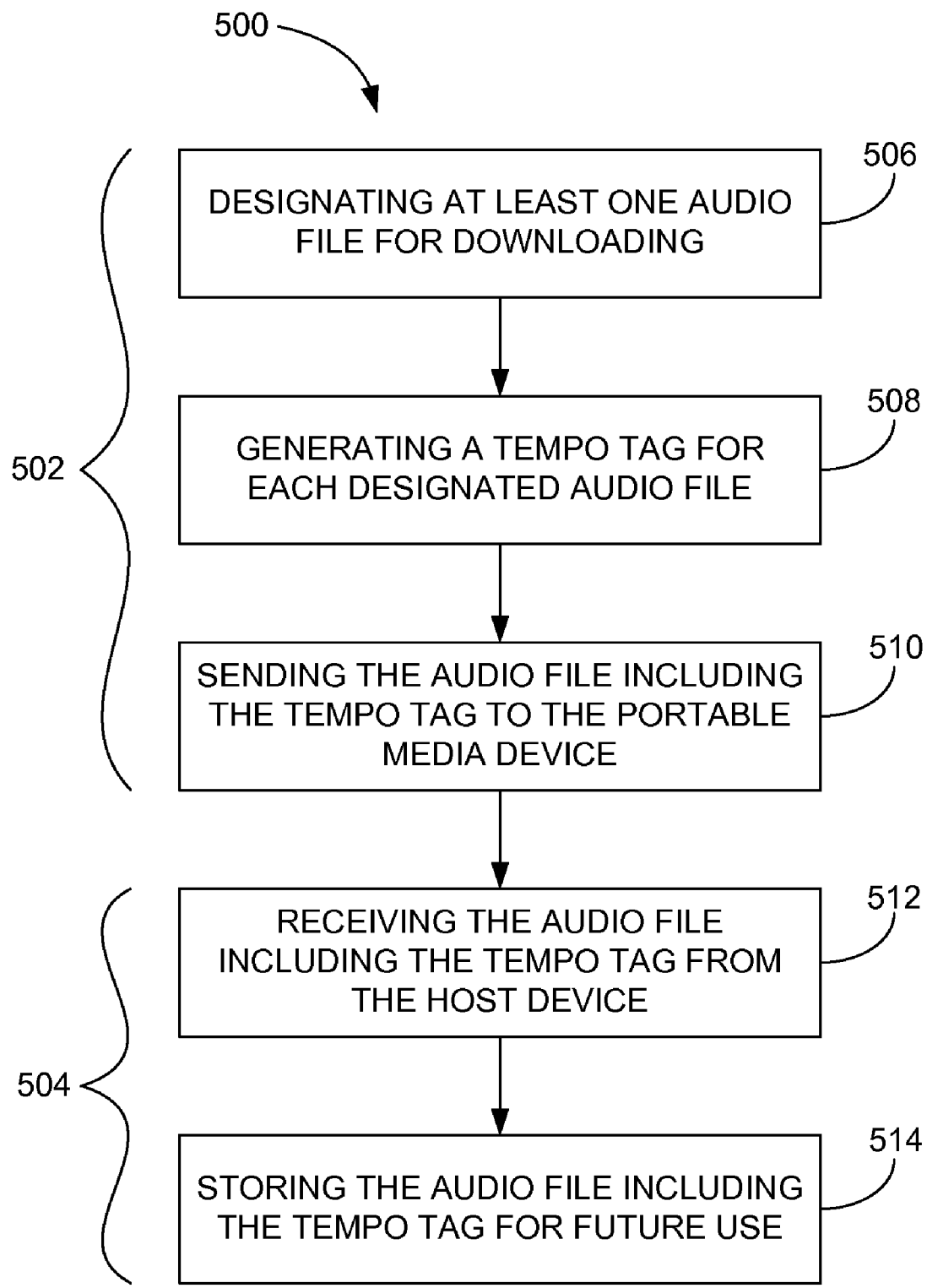
FIG. 16 is method of transferring data between a host device and a portable media device, in accordance with one embodiment of the present invention.

FIG. 16 is method 500 of transferring data between a host device and a portable media device, in accordance with one embodiment of the present invention. The method 500 is broken up into two steps. A first step 502 is performed at the host device, and a second step 504 is performed at the portable media device. The first step 502 includes blocks 506-510, the second step 504 includes blocks 512 and 514. The method 500 generally begins at block 506 where at least one audio file is designated for downloading to the portable media device. Thereafter, in block 508, a tempo tag is generated for each designated audio file. Each tempo tag indicates the tempo of the audio track associated with the audio file. Thereafter, in block 510, the audio file including the audio track and the tempo tag are sent to the portable media device.

Following block 510, the method proceeds to block 512 where the audio file including the audio track and tempo tag are received at the portable media device. Thereafter, in block 514, the audio file including the audio track and the tempo tag are stored at the portable media device. Once stored, the tempo tag may be used by the portable media device to help select appropriate songs when a desired tempo is designated. For example, the media device may compare the desired tempo to the tempo tag in order to determine if the audio track should be played. It should be noted that the tempo tag associated with an audio track can be provided in the audio file or separate from the audio file.

Figure 17:
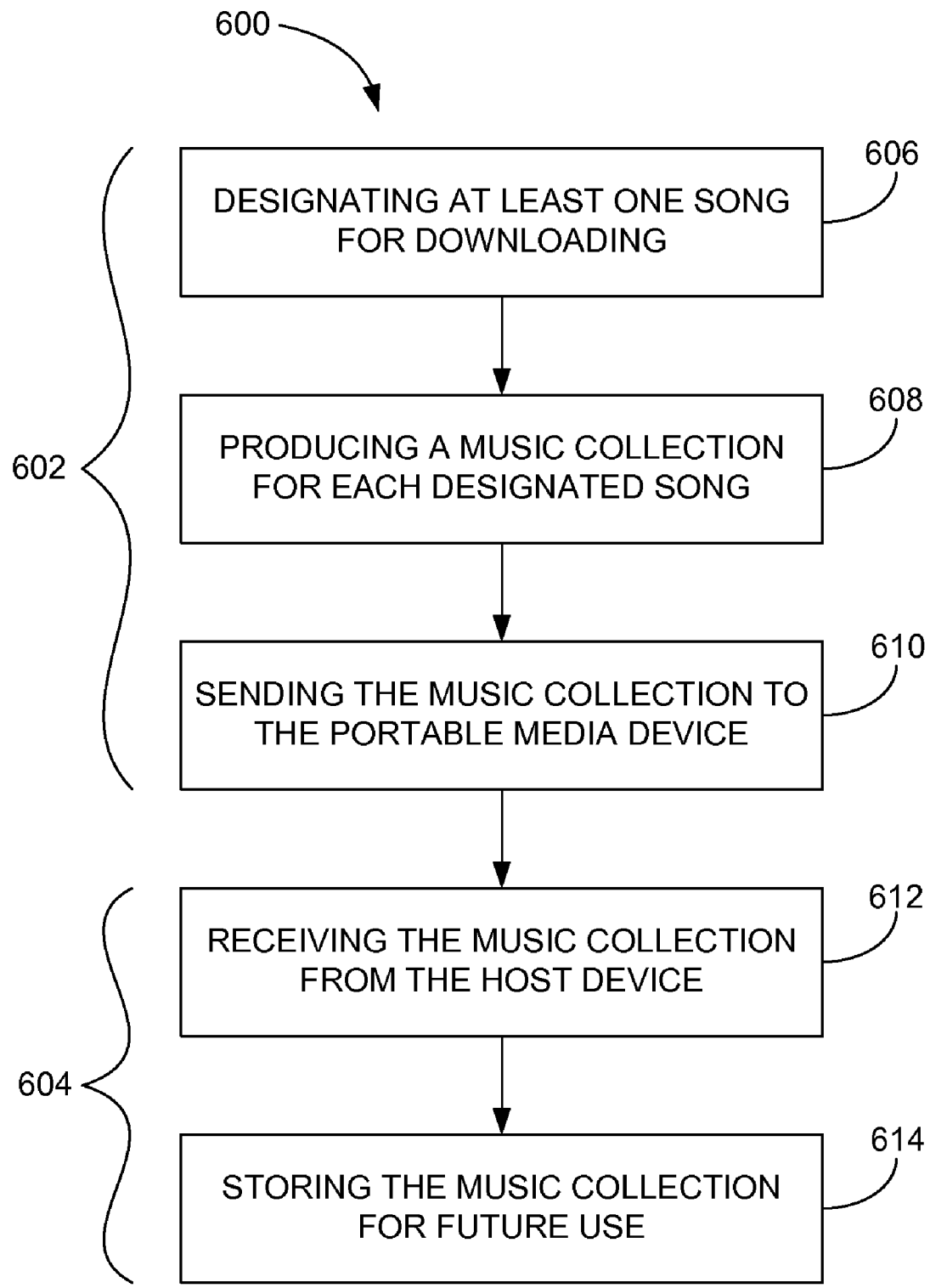
FIG. 17 is method of transferring data between a host device and a portable media device, in accordance with one embodiment of the present invention.

FIG. 17 is method 600 of transferring data between a host device and a portable media device, in accordance with one embodiment of the present invention. The method 600 is broken up into two steps. A first step 602 is performed at the host device, and a second step 604 is performed at the portable media device. The first step 602 includes blocks 606-610, the second step 604 includes blocks 612 and 614. The method 600 generally begins at block 606 where at least one song is designated for downloading to the portable media device. Thereafter, in block 608, a music collection for each designated song is produced. Each music collection contains the original version of the designated song as well as new versions of the designated song. Each new version has been reformatted to have a different tempo. In some cases, each song includes a tempo tag. Thereafter, in block 610, the music collection is sent to the portable media device.

Following block 610, the method proceeds to block 612 where music collection is received at the portable media device. Thereafter, in block 614, the music collection is stored at the portable media device. Once stored, the entire music collection may be used by the portable media device when selecting songs in accordance with a desired tempo range. In some cases, the music collection includes tags that indicate that the songs are tempo low, tempo medium or tempo high.

Figures 18, 19, 20, 21:
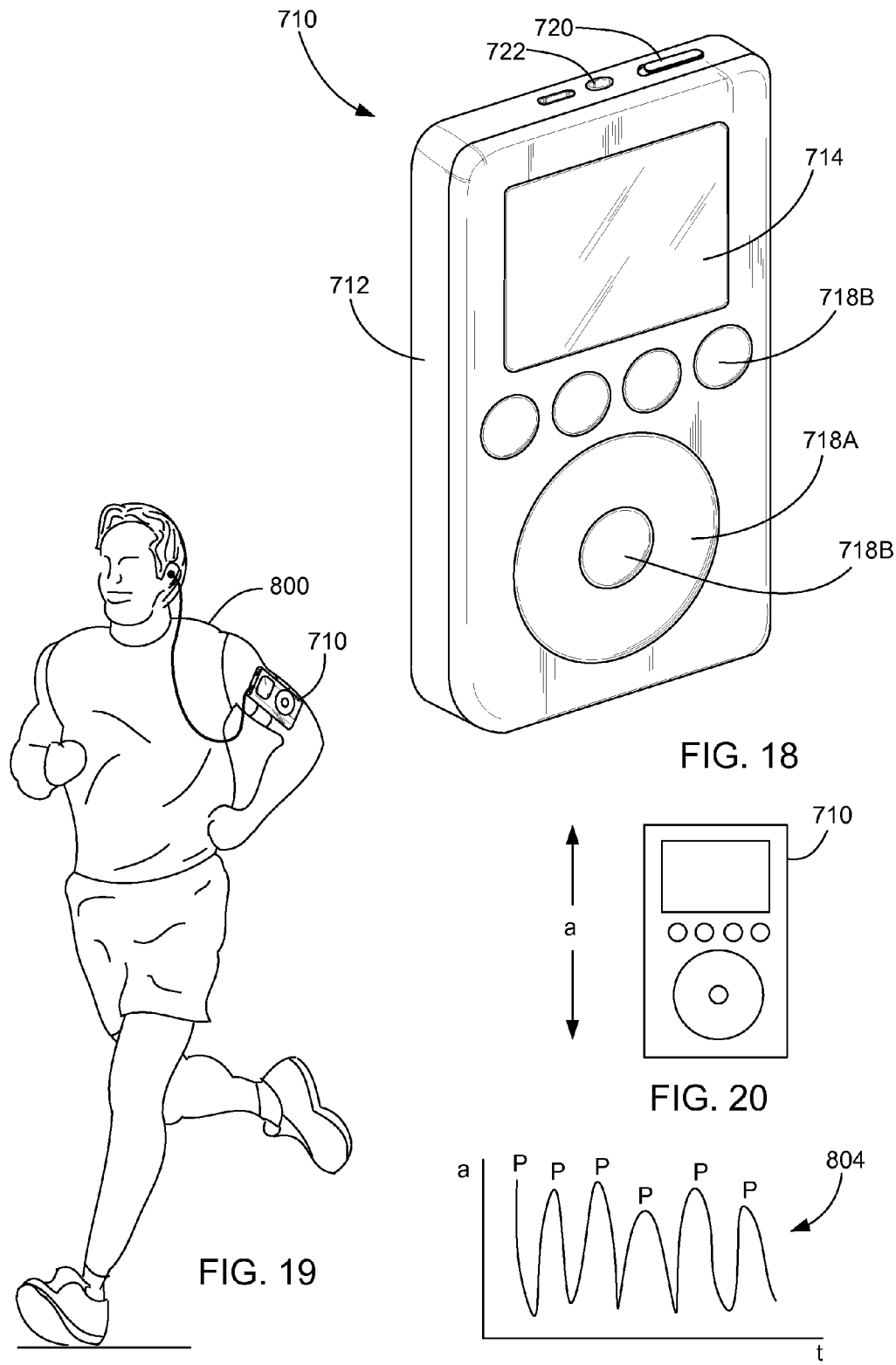
FIG. 18 is perspective view of a hand-held computing device, in accordance with one embodiment of the present invention.
FIG. 19 shows a user jogging with a music player attached to the arm, in accordance with one embodiment of the present invention.
FIG. 20 shows a music player moving up and down in accordance with a user's steps, in accordance with one embodiment of the present invention.
FIG. 21 shows an exemplary signal produced by an accelerometer, in accordance with one embodiment of the present invention.

FIG. 18 is perspective view of a hand-held computing device 710, in accordance with one embodiment of the present invention. The computing device 710 is capable of processing data and more particularly media such as audio, video, images, etc. By way of example, the computing device 710 may generally correspond to a music player, video player, game player, video player, camera, cell phone, personal digital assistant (PDA), and/or the like. With regards to being hand-held, the computing device 710 can be operated solely by the user's hand(s), i.e., no reference surface such as a desktop is needed. In some cases, the hand-held device is sized for placement into a pocket of the user. By being pocket sized, the user does not have to directly carry the device and therefore the device can be taken almost anywhere the user travels (e.g., the user is not limited by carrying a large, bulky and heavy device).

As shown, the computing device 710 includes a housing 712 that encloses and supports internally various electrical components (including integrated circuit chips and other circuitry) to provide computing operations for the device. The integrated circuit chips and other circuitry may include a microprocessor, memory, a battery, and various input/output (I/O) support circuitry. In most cases, the microprocessor executes instructions and carries out operations associated with the computing device. For example, using instructions retrieved for example from memory, the microprocessor may control the reception and manipulation of input and output data between components of the computing device 710. In fact, the microprocessor may work with an operating system to execute computer code and produce and use data stored in memory. By way of example, the memory may include a hard drive, flash memory, Read-Only Memory (ROM), Random-Access Memory (RAM) and/or the like.

The computing device 710 also includes a display 714. The display 714, which is assembled within the housing 712 and which is visible through an opening in the housing 712, is used to display a graphical user interface (GUI) as well as other information to the user (e.g., text, objects, graphics). The display 714 generally takes the form of a flat panel display such as a liquid crystal display (LCD).

The computing device 710 also includes one or more input devices 718 configured to transfer data from the outside world into the computing device 710. The input devices 718 may for example be used to perform tracking/scrolling, to make selections or to issue commands in the computing device 710. By way of example, the input devices 718 may correspond to keypads, joysticks, touch screens, touch pads, track balls, wheels, buttons, switches, and/or the like. In the illustrated embodiment, the computing device 710 includes a touch pad 718A and a plurality of buttons 718B, which are assembled within the housing 712 and which are accessible through openings in the housing 712.

The computing device 710 may include one or more switches 720 including power switches, hold switches, and the like. Furthermore, the device 710 may include one or more connectors 722 including data ports, jacks, power terminals, etc.

In the illustrated embodiment, the computing device 710 is a pocket sized hand-held music player that allows a user to store a large collection of music, and to listen to this music on the go (e.g., while working, traveling, exercising, etc.). In the case of a music player, the memory may contain music playing software, playlists containing a plurality of songs, etc. Furthermore, the GUI may visually provide menus, playlists, music controls and/or the like to the user. Moreover, the touch pad may provide scrolling functions, which allow a user to traverse through menus or playlists on the GUI and the buttons may provide button functions that open a menu, play a song, fast forward through a song, seek through a menu and/or the like. In addition, the music player typically includes an audio jack for outputting audio and a data port for transmitting and receiving audio data (and other data.) to and from a host device. By way of example, the music player may correspond to the iPod series MP3 players manufactured by Apple Inc. of Cupertino, Calif.

In one embodiment, the music player includes an accelerometer inside the housing. By way of example, the accelerometer may be model ADXL311 manufactured by Analog Devices of Norwood, Mass. The accelerometer may for example be attached to the main PCB that includes the major circuitry components of the music player including for example the processor, memory and other IC chips. The accelerometer as the term used herein covers both a raw accelerometer and any accelerometer that also includes other components such as an ASIC. Because the music player is typically worn during use as for example using a belt clip or arm band (fixed to the user), the accelerometer measures the motion of the user and produces a signal indicative thereof. See for example FIG. 19, which shows a user 800 jogging with a music player 710 attached to the arm, FIG. 20, which shows the music player 710 moving up and down when the user takes steps, and FIG. 21, which shows an exemplary signal 802 produced by the accelerometer (the accelerometer converts the acceleration of the user into an electronic signal).

The tempo of the user event (jogging) can be extracted from the accelerometer signal. For example, referring to FIG. 20, each peak P in the acceleration signal may represent a consecutive step, and therefore the number of steps in a given time frame may indicate the beats per minute or tempo of the jogging steps. The extraction can be performed by the accelerometer as for example via an ASIC or it can be performed by the main processor or some sub processor of the music player 710.

In some cases, the raw accelerometer data is converted, filtered or transformed into tempo data. Because the accelerometer measures all motion not just the steps, the step information typically needs to be separated from the other motion information to produce an accurate tempo reading. As should be appreciated, large scale movements such as steps may produce low frequency information and small scale movements such as vibrations may produce high frequency information. The high frequency information can be filtered out thereby leaving only low frequency information indicative of the large scale movements (e.g., steps). The filtered information can then be converted into tempo information.

FIGS. 22 and 23 are side elevation views of the hand-held computing device 710 shown in FIG. 18, in accordance with different embodiments of the present invention. As shown in both figures, the computing device 710 includes a housing 712 that defines an internal chamber 730 for placing the components 732 of the computing device 710. The components 732 may for example include a printed circuit board 734 that provides a central structure for carrying and connecting the operational components 736 and supporting them when assembled inside the housing 710. The PCB 734 is generally attached to the housing 710 and typically contains various integrated circuit chips and other circuitry that provide computing operations for the computing device 710. The printed circuit board 734 may for example include a microprocessor, memory, a data port, and various switches. The internal chamber 732 may also contain a display, a hard drive, a battery and an audio subassembly, each of which is operatively coupled to the printed circuit board 734 and its various components through interconnecting circuitry.

In accordance with one embodiment of the present invention, an accelerometer 740 is mounted inside the housing 710 within the internal chamber 732. This is typically done to reduce cost and complexity, and in some cases this may also help reduce unwanted high frequency content (e.g., the mass of the computing device may mechanically filter out the high frequency content). As shown in FIG. 21, the accelerometer 740 is mounted onto the housing 710 or some structural element of the housing 710. As shown in FIG. 22, the accelerometer 740 is mounted securely onto the PCB 734. As a result of mounting the accelerometer 740 directly or indirectly to the housing 710, the accelerometer 740 moves with the movement of the housing 710. The accelerometer 740 therefore measures the acceleration of the computing device 710 as it is moved.

While this invention has been described in terms of several preferred embodiments, there are alterations, permutations, and equivalents, which fall within the scope of this invention. For example, although the media items of emphasis in several of the above embodiments were audio items (e.g., audio files or songs), the media items are not limited to audio items. For example, the media item can alternatively pertain to videos (e.g., movies) or images (e.g., photos). Furthermore, the various aspects, embodiments, implementations or features of the invention can be used separately or in any combination.

It should also be noted that there are many alternative ways of implementing the methods and apparatuses of the present invention. For example, the invention is preferably implemented by software, but can also be implemented in hardware or a combination of hardware and software. The invention can also be embodied as computer readable code on a computer readable medium. The computer readable medium is any data storage device that can store data, which can thereafter be read by a computer system. Examples of the computer readable medium include read-only memory, random-access memory, CD-ROMs, DVDs, magnetic tape, optical data storage devices, and carrier waves. The computer readable medium can also be distributed over network-coupled computer systems so that the computer readable code is stored and executed in a distributed fashion.

It is therefore intended that the following appended claims be interpreted as including all such alterations, permutations, and equivalents as fall within the true spirit and scope of the present invention.

The invention claimed is:

1. A method for playing a media item on a portable media device, the method comprising:
   determining a current pace of exercise of a user of the portable media device;
   determining a desired pace of exercise for the user;
   selecting a item that, among all media items on the portable media device, has the tempo that best matches both the desired pace of exercise and the user's current pace of exercise; and
   dynamically adjusting the tempo of the selected media item to best fit both the desired pace of exercise and the current pace of exercise.

2. The method of claim 1, wherein a tempo corresponds to the desired pace of exercise if the tempo is a multiple of the desired pace of exercise.

3. The method of claim 1, wherein a tempo corresponds to the desired pace of exercise if the tempo is a divisor of the desired pace of exercise.

4. The method of claim 1, wherein the desired pace of exercise is determined by a music manager based on a set of rules.

5. A media player for modifying a song based on an exercise regime, the media player comprising:
   a file system operable to store a plurality of songs having tempo tags associated with each of the songs, wherein each tempo tag represents an exact tempo value of a song from the plurality of songs, and an exercise regime; and
   a processor coupled to the file system and operable to:
      download multiple versions of the same song from a server computer to a portable media device, wherein the multiple versions represent the same song in different tempos;
      determine a desired tempo of a portion of an exercise regime;
      compare the desired tempo to at least one of the stored tempo tags; and
      select, at the portable media device, a song from the plurality of songs having a tempo that best matches both the desired tempo and a current pace of exercise, so that, when dynamically adjusted, the selected song has sufficient length to play for the entire duration of the portion of the exercise routine; and
      dynamically adjust the tempo of the selected song to best match both the desired tempo and the current pace of exercise.

6. The media player of claim 5, further comprising an input device operable to receive a user input selecting an exercise regime.

7. The media player of claim 5, further comprising input circuitry operable to receive the plurality of tempo tags from a host computer.

8. The media player of claim 5, further comprising a media database operable to store the plurality of tempo tags.

9. The media player of claim 5, further comprising a CODEC operable to produce an analog output signal based on the selected song.

10. A method for modifying a media item based on an exercise routine, the method comprising:
    downloading multiple versions of the same media item from a server computer to a portable media device, wherein the multiple versions represent the same media item in different tempos;
    determining a desired tempo of a portion of an exercise regime;
    comparing the desired tempo to at least one of the stored tempo tags; and
    selecting, at the portable media device, a media item from the plurality of media items having a tempo that best matches both the desired tempo and a current pace of exercise, so that, when dynamically adjusted, the selected media item has sufficient length to play for the entire duration of the portion of the exercise routine; and
    dynamically adjusting the tempo of the selected media item to best match both the desired tempo and the current pace of exercise.

11. The method of claim 10, wherein the media item is a video.

12. The method of claim 10, wherein the media item is a song.

13. The method of claim 10, wherein the comparing and dynamically adjusting is performed continuously by a media manager on the portable media device.

14. A computer readable medium for storing in non-transitory tangible form computer instructions executable by a processor for playing a media item on a portable media device, the computer readable medium comprising:
- computer code for determining a current pace of movement of a user of the portable media device;
- computer code for determining a desired pace of movement for the user;

selecting the version of the media item that, among all versions of the media item on the portable media device, has the tempo that best matches both the desired pace of movement and the user's current pace of movement; and
- computer code for dynamically adjusting the tempo of the selected version of the media item to best fit both the desired pace of movement and the current pace of movement.

15. The computer readable medium of claim 14, wherein the media item has a corresponding tempo tag indicating the tempo of the audio the media item.

16. The computer readable medium of claim 14, wherein the computer code for dynamically adjusting the tempo of the media item to fit the desired pace of movement includes computer code for controlling a digital signal processor to adjust the tempo.

17. The computer readable medium of claim 14, wherein the computer code for dynamically adjusting the tempo of the media item to fit the desired pace of movement includes computer code for performing phase vocoding.

18. An apparatus for playing a media item on a portable media device, the method comprising:
- means for downloading multiple versions of the media item from a server computer, wherein the multiple versions represent the media item in different tempos;
- means for determining a current rhythm of movement of a user of the portable media device;
- means for determining a desired rhythm of movement for the user;
- means for selecting a media item associated with a tempo tag that has a tempo that best matches both the desired rhythm of movement and the user's current rhythm of movement; and
- means for dynamically adjusting the tempo of the media item to best fit both the desired rhythm of movement and the current rhythm of movement.

19. The apparatus of claim 18, wherein the means for dynamically adjusting includes a phase vocoder that includes elements of linear predictive coding to use continuous and overlapping Fourier transforms of a media item for time stretching.

20. The apparatus of claim 18, wherein the means for dynamically adjusting includes a sliding fast Fourier transform (SFFT) processor.

21. The apparatus of claim 18, wherein the means for selecting includes means for selecting a media item associated with a tempo tag from a playlist that has a tempo corresponding to the desired rhythm of movement.

* * * * *